US012004771B1

(12) United States Patent
Mustapha et al.

(10) Patent No.: US 12,004,771 B1
(45) Date of Patent: Jun. 11, 2024

(54) ROTATIONAL ATHERECTOMY DEVICES AND METHODS

(71) Applicant: Cardio Flow, Inc., St. Paul, MN (US)

(72) Inventors: Jihad A. Mustapha, Ada, MI (US); Gary M. Petrucci, Long Lake, MN (US); Albert Selden Benjamin, St. Paul, MN (US); Ryan D. Welty, Blaine, MN (US)

(73) Assignee: Cardio Flow, Inc., St. Paul, MN (US)

( * ) Notice: Subject to any disclaimer, the term of this patent is extended or adjusted under 35 U.S.C. 154(b) by 0 days.

(21) Appl. No.: 18/523,683

(22) Filed: Nov. 29, 2023

Related U.S. Application Data

(60) Provisional application No. 63/542,438, filed on Oct. 4, 2023, provisional application No. 63/523,583, filed on Jun. 27, 2023.

(51) Int. Cl.
*A61B 17/3207* (2006.01)

(52) U.S. Cl.
CPC .. *A61B 17/320758* (2013.01); *A61B 17/3207* (2013.01); *A61B 17/320725* (2013.01); *A61B 2017/320766* (2013.01)

(58) Field of Classification Search
CPC .... A61B 17/320725; A61B 17/320766; A61B 17/32002; A61B 17/3207; A61B 17/320758
See application file for complete search history.

(56) References Cited

U.S. PATENT DOCUMENTS

| 1,431,416 A | 10/1922 | Parsons et al. |
| 1,916,085 A | 6/1933 | Summers et al. |
| 2,495,316 A | 1/1950 | Clark et al. |
| 3,929,129 A | 12/1975 | Archambault |
| 4,445,509 A | 5/1984 | Auth |
| 4,445,892 A | 5/1984 | Hussein et al. |
| 4,620,320 A | 10/1986 | Sullivan |
| 4,646,736 A | 3/1987 | Auth |
| 4,762,130 A | 8/1988 | Fogarty et al. |
| 4,772,258 A | 9/1988 | Marangoni et al. |
| 4,784,636 A | 11/1988 | Rydell |

(Continued)

FOREIGN PATENT DOCUMENTS

| CN | 104955406 | 9/2015 |
| DE | 20305953 | 10/2003 |

(Continued)

OTHER PUBLICATIONS

"Declaration of Dr. Morten Olgaard Jensen," IPIPR2018-01658, Exhibit 1002, dated Sep. 4, 2018.

(Continued)

*Primary Examiner* — Anh T Dang
(74) *Attorney, Agent, or Firm* — Fish & Richardson P.C.

(57) ABSTRACT

Some embodiments of a rotational atherectomy device can remove (partially or completely) stenotic lesions in blood vessels by rotating one or more abrasive elements in an orbital path to abrade and breakdown the lesion. In particular implementations, multiple abrasive elements are arranged along a distal portion of a drive shaft with an improved configuration so as to facilitate both efficient navigation into smaller blood vessels below the ankle or in the heart and effective orbital paths for abrading stenotic material in such smaller vessels.

19 Claims, 11 Drawing Sheets

(56) References Cited

U.S. PATENT DOCUMENTS

| | | |
|---|---|---|
| 4,870,953 A | 10/1989 | DonMicheal et al. |
| 4,887,469 A | 12/1989 | Shoptaw |
| 4,931,635 A | 6/1990 | Toyama |
| 4,950,238 A | 8/1990 | Sullivan |
| 4,990,134 A | 2/1991 | Auth et al. |
| 5,014,681 A | 5/1991 | Neeman et al. |
| 5,100,425 A | 3/1992 | Fischell et al. |
| 5,127,902 A | 7/1992 | Fischell et al. |
| 5,181,920 A | 1/1993 | Mueller et al. |
| 5,213,576 A | 5/1993 | Abiuso |
| 5,213,577 A | 5/1993 | Kratzer |
| 5,217,474 A | 6/1993 | Zacca et al. |
| 5,242,460 A | 9/1993 | Klein et al. |
| 5,250,059 A | 10/1993 | Andreas et al. |
| 5,250,060 A | 10/1993 | Carbo et al. |
| 5,273,526 A | 12/1993 | Dance et al. |
| 5,308,354 A | 5/1994 | Zacca et al. |
| 5,312,427 A | 5/1994 | Shturman |
| 5,314,407 A | 5/1994 | Auth |
| 5,314,438 A | 5/1994 | Shturman |
| 5,342,292 A | 8/1994 | Nita et al. |
| 5,361,285 A | 11/1994 | Formanek et al. |
| 5,370,653 A | 12/1994 | Cragg |
| 5,435,009 A | 7/1995 | Schild |
| 5,458,575 A | 10/1995 | Wang |
| 5,490,859 A | 2/1996 | Mische et al. |
| 5,512,044 A | 4/1996 | Duer |
| 5,556,389 A | 9/1996 | Liprie |
| 5,584,843 A | 12/1996 | Wulfman et al. |
| 5,649,941 A | 7/1997 | Lary |
| 5,681,336 A | 10/1997 | Clement et al. |
| 5,730,717 A | 3/1998 | Gelbfish |
| 5,766,192 A | 6/1998 | Zacca et al. |
| 5,771,895 A | 6/1998 | Slager |
| 5,816,923 A | 10/1998 | Milo et al. |
| 5,836,957 A | 11/1998 | Schulz |
| 5,843,103 A | 12/1998 | Wulfman |
| 5,868,708 A | 2/1999 | Hart et al. |
| 5,893,857 A | 4/1999 | Shturman |
| 6,010,533 A | 1/2000 | Pope et al. |
| 6,015,420 A | 1/2000 | Wulfman |
| 6,022,363 A | 2/2000 | Walker et al. |
| 6,024,749 A | 2/2000 | Shturman et al. |
| 6,030,401 A | 2/2000 | Marino |
| 6,066,152 A | 5/2000 | Strauss et al. |
| 6,077,282 A | 6/2000 | Shturrnan et al. |
| 6,096,054 A | 8/2000 | Wyzgala et al. |
| 6,132,444 A | 10/2000 | Shturman et al. |
| 6,135,982 A | 10/2000 | Campbell |
| 6,146,395 A | 11/2000 | Kanz |
| 6,152,911 A | 11/2000 | Giannoble |
| 6,156,048 A | 12/2000 | Wulfman |
| 6,217,595 B1 | 4/2001 | Shturman |
| 6,241,706 B1 | 6/2001 | Leschinsky et al. |
| 6,270,465 B1 | 8/2001 | Keith et al. |
| 6,416,526 B1 | 7/2002 | Wyzgala |
| 6,482,216 B1 | 11/2002 | Hiblar et al. |
| 6,485,500 B1 | 11/2002 | Kokish et al. |
| 6,491,660 B2 | 12/2002 | Guo et al. |
| 6,494,890 B1 | 12/2002 | Shturman et al. |
| 6,497,711 B1 | 12/2002 | Plaia |
| 6,565,588 B1 | 5/2003 | Clement et al. |
| 6,626,861 B1 | 9/2003 | Hart |
| 6,685,718 B1 | 2/2004 | Wyzgala et al. |
| 6,733,513 B2 | 5/2004 | Boyle et al. |
| 6,805,485 B2 | 10/2004 | Hogan et al. |
| 6,852,118 B2 | 2/2005 | Shturman et al. |
| 6,955,661 B1 | 10/2005 | Herweck et al. |
| 7,252,674 B2 | 8/2007 | Wyzgala |
| 7,666,202 B2 | 2/2010 | Prudnikov |
| 7,766,049 B2 | 8/2010 | Miller |
| 8,109,954 B2 | 2/2012 | Shturman |
| 8,109,955 B2 | 2/2012 | Shturman |
| 8,137,369 B2 | 3/2012 | Shturman |
| 8,142,458 B2 | 3/2012 | Shturman |
| 8,147,507 B2 | 4/2012 | Shturman |
| 8,157,825 B2 | 4/2012 | Shturman |
| 8,177,801 B2 | 5/2012 | Kallok |
| 8,348,965 B2 | 1/2013 | Prudnikov |
| 8,353,923 B2 | 1/2013 | Shturman |
| 8,388,636 B2 | 3/2013 | Shturman |
| 8,388,637 B2 | 3/2013 | Shturman |
| 8,454,638 B2 | 6/2013 | Shturman |
| 8,465,510 B2 | 6/2013 | Shturman |
| 8,496,678 B2 | 7/2013 | Shturman |
| 8,500,764 B2 | 8/2013 | Shturman |
| 8,500,765 B2 | 8/2013 | Shturman |
| 8,597,313 B2 | 12/2013 | Thatcher |
| 8,628,550 B2 | 1/2014 | Narveson |
| 8,663,195 B2 | 3/2014 | Shturman |
| 8,663,260 B2 | 3/2014 | Shturman |
| 8,663,261 B2 | 3/2014 | Shturman |
| 8,936,589 B2 | 1/2015 | Shturman |
| 9,089,362 B2 | 7/2015 | Shturman |
| 9,192,405 B2 | 11/2015 | Shturman |
| 9,211,138 B2 | 12/2015 | Shturman |
| 9,237,903 B2 | 1/2016 | Shturman |
| 9,289,230 B2 | 3/2016 | Cambronne |
| 9,333,006 B2 | 5/2016 | Shturman |
| 9,364,256 B2 | 6/2016 | Shturman |
| 9,387,006 B2 | 7/2016 | Shturman |
| 9,597,109 B2 | 3/2017 | Shturman |
| 9,737,329 B2 | 8/2017 | Shturman |
| 9,757,144 B2 | 9/2017 | Shturman |
| 9,788,853 B2 | 10/2017 | Robinson |
| 9,883,886 B2 | 2/2018 | Shturman |
| 10,052,122 B2 | 8/2018 | Higgins |
| 10,052,124 B2 | 8/2018 | Cambronne |
| 10,064,646 B2 | 9/2018 | Cambronne |
| 10,327,803 B2 | 6/2019 | Robinson et al. |
| 10,335,187 B2 | 7/2019 | Benjamin et al. |
| 10,368,901 B2 | 8/2019 | Robinson et al. |
| 10,441,312 B2 | 10/2019 | Shturman |
| 10,463,390 B1 | 11/2019 | Robinson et al. |
| 10,470,794 B2 | 11/2019 | Robinson et al. |
| 10,478,215 B2 | 11/2019 | Robinson et al. |
| 10,478,216 B2 | 11/2019 | Robinson et al. |
| 10,478,217 B2 | 11/2019 | Robinson et al. |
| 10,499,946 B2 | 12/2019 | Robinson et al. |
| 10,517,631 B2 | 12/2019 | Cambronne |
| 10,517,634 B2 | 12/2019 | Benjamin et al. |
| 10,524,826 B1 | 1/2020 | Kallok et al. |
| 10,639,062 B2 | 5/2020 | Piippo Svendsen et al. |
| 10,639,063 B2 | 5/2020 | Piippo Svendsen et al. |
| 10,639,064 B2 | 5/2020 | Piippo Svendsen et al. |
| 11,147,582 B2 | 10/2021 | Kallok et al. |
| 11,213,314 B1 | 1/2022 | Robinson et al. |
| 11,253,290 B2 | 2/2022 | Kallok et al. |
| 11,317,941 B2 | 5/2022 | Benjamin et al. |
| 11,457,946 B1 | 10/2022 | Robinson et al. |
| 11,812,988 B2 | 11/2023 | Kallok et al. |
| 2002/0007190 A1 | 1/2002 | Wulfman |
| 2002/0013600 A1 | 1/2002 | Scribner |
| 2002/0029056 A1 | 3/2002 | Hall |
| 2002/0082547 A1 | 6/2002 | Deniega |
| 2002/0099367 A1 | 7/2002 | Zihong |
| 2002/0138088 A1 | 9/2002 | Nash |
| 2002/0151918 A1 | 10/2002 | Lafontaine |
| 2002/0188276 A1 | 12/2002 | Evans |
| 2003/0078606 A1 | 4/2003 | Lafontaine |
| 2003/0114869 A1 | 6/2003 | Nash |
| 2003/0125756 A1 | 7/2003 | Shturman |
| 2003/0139689 A1 | 7/2003 | Shturman |
| 2003/0199889 A1 | 10/2003 | Kanz |
| 2004/0098014 A1 | 5/2004 | Flugelman |
| 2004/0158270 A1 | 8/2004 | Wyzgala |
| 2005/0154416 A1 | 7/2005 | Herweck |
| 2005/0209615 A1 | 9/2005 | Prudnikov |
| 2005/0228402 A1 | 10/2005 | Hofmann |
| 2005/0240146 A1 | 10/2005 | Nash |
| 2005/0245864 A1 | 11/2005 | O'Brien |
| 2005/0256461 A1 | 11/2005 | Difiore |
| 2006/0189929 A1 | 8/2006 | Lary |
| 2006/0258976 A1 | 11/2006 | Shturman |

(56) References Cited

U.S. PATENT DOCUMENTS

| | | |
|---|---|---|
| 2007/0007190 A1 | 1/2007 | Pethke |
| 2007/0066888 A1 | 3/2007 | Maschke |
| 2008/0004643 A1 | 1/2008 | Schur |
| 2008/0097498 A1 | 4/2008 | Shimizu |
| 2008/0119946 A1 | 5/2008 | Nugent et al. |
| 2008/0161840 A1 | 7/2008 | Osiroff |
| 2008/0306498 A1 | 12/2008 | Thatcher |
| 2008/0319415 A1 | 12/2008 | Shturman |
| 2009/0018564 A1 | 1/2009 | Shturman |
| 2009/0069829 A1 | 3/2009 | Shturman |
| 2009/0105736 A1 | 4/2009 | Prudnikov |
| 2009/0182359 A1 | 7/2009 | Shturman |
| 2009/0264908 A1 | 10/2009 | Kallok |
| 2009/0312777 A1 | 12/2009 | Shturman |
| 2009/0318942 A1 | 12/2009 | Shturman |
| 2009/0326568 A1 | 12/2009 | Shturman |
| 2010/0010522 A1 | 1/2010 | Shturman |
| 2010/0049226 A1 | 2/2010 | Shturman |
| 2010/0121361 A1 | 5/2010 | Plowe |
| 2010/0211088 A1 | 8/2010 | Narveson |
| 2011/0009888 A1 | 1/2011 | Shturman |
| 2011/0054332 A1 | 3/2011 | Shturman |
| 2011/0213391 A1 | 9/2011 | Rivers |
| 2012/0035633 A1 | 2/2012 | Shturman |
| 2012/0109170 A1 | 5/2012 | Shturman |
| 2012/0150207 A1 | 6/2012 | Shturman |
| 2012/0172903 A1 | 7/2012 | Shturman |
| 2012/0178986 A1 | 7/2012 | Campbell |
| 2012/0191113 A1 | 7/2012 | Shturman |
| 2012/0213391 A1 | 8/2012 | Usami |
| 2013/0178881 A1 | 7/2013 | Shturman |
| 2013/0204280 A1 | 8/2013 | Shturman |
| 2013/0245654 A1 | 9/2013 | Shturman |
| 2013/0274773 A1 | 10/2013 | Shturman |
| 2013/0296904 A1 | 11/2013 | Shturman |
| 2013/0296905 A1 | 11/2013 | Shturman |
| 2013/0310589 A1 | 11/2013 | van Leonard |
| 2013/0310859 A1 | 11/2013 | Shturman |
| 2013/0333365 A1 | 12/2013 | Silet |
| 2014/0081298 A1 | 3/2014 | Cambonne |
| 2014/0180317 A1 | 6/2014 | Shturman |
| 2014/0180318 A1 | 6/2014 | Shturman |
| 2014/0180319 A1 | 6/2014 | Shturman |
| 2014/0296888 A1 | 10/2014 | Schur |
| 2015/0080795 A1 | 3/2015 | Mattison |
| 2015/0094733 A1 | 4/2015 | Shiber |
| 2015/0164540 A1 | 6/2015 | Higgins et al. |
| 2015/0196320 A1 | 7/2015 | Robinson |
| 2015/0313629 A1 | 11/2015 | Shturman |
| 2016/0199093 A1 | 7/2016 | Cambronne |
| 2016/0346003 A1 | 12/2016 | Grothe |
| 2017/0056040 A1 | 3/2017 | Vetter |
| 2017/0290603 A1 | 10/2017 | Piippo |
| 2018/0064464 A1 | 3/2018 | Robinson |
| 2018/0235652 A1 | 8/2018 | Benjamin |
| 2018/0263654 A1 | 9/2018 | Steele |
| 2019/0053823 A1 | 2/2019 | Benjamin et al. |
| 2019/0083126 A1 | 3/2019 | Benjamin et al. |
| 2019/0090901 A1* | 3/2019 | Piippo Svendsen ........................ A61B 17/320758 |
| 2019/0262035 A1* | 8/2019 | Gurm .............. A61B 17/320758 |
| 2019/0298406 A1 | 10/2019 | Lee et al. |
| 2019/0380737 A1 | 12/2019 | Kallok et al. |
| 2020/0046403 A1* | 2/2020 | Piippo Svendsen ........................ A61B 17/32002 |
| 2020/0129203 A1 | 4/2020 | Benjamin et al. |
| 2020/0138474 A1 | 5/2020 | Kallok et al. |
| 2020/0155194 A1* | 5/2020 | Schneider ...... A61B 17/320725 |
| 2022/0110654 A1 | 4/2022 | Robinson et al. |
| 2022/0133345 A1 | 5/2022 | Kallok et al. |
| 2022/0218386 A1 | 7/2022 | Benjamin et al. |
| 2023/0116977 A1 | 4/2023 | Robinson et al. |
| 2024/0074783 A1 | 3/2024 | Kallok et al. |

FOREIGN PATENT DOCUMENTS

| | | |
|---|---|---|
| EP | 0419154 | 3/1991 |
| EP | 0479433 | 4/1992 |
| EP | 0820729 | 1/1998 |
| EP | 1405797 | 4/2004 |
| EP | 1820458 | 8/2007 |
| EP | 3105978 | 12/2016 |
| FR | 1595757 | 6/1970 |
| GB | 854573 | 11/1960 |
| GB | 2039208 | 8/1980 |
| GB | 2271060 | 4/1994 |
| GB | 2357573 | 6/2001 |
| GB | 2426458 | 11/2006 |
| WO | WO 1997/014470 | 4/1997 |
| WO | WO 1998/050101 | 11/1998 |
| WO | WO 1999/044513 | 9/1999 |
| WO | WO 2001/015759 | 3/2001 |
| WO | WO 2002/009599 | 2/2002 |
| WO | WO 2003/061457 | 7/2003 |
| WO | WO 2006/126076 | 11/2006 |
| WO | WO 2006/126175 | 11/2006 |
| WO | WO 2006/126176 | 11/2006 |
| WO | WO 2008/006704 | 1/2008 |
| WO | WO 2014/042752 | 3/2014 |

OTHER PUBLICATIONS

"Declaration of Dr. Morten Olgaard Jensen," IPR2018-01549, Exhibit 1002, dated Aug. 15, 2018.
"Declaration of Kristina Rouw, Ph.D," IPR2018-01549, Exhibit 2001, dated Nov. 29, 2018.
"Declaration of Kristina Rouw, Ph.D," IPR2018-01658, Exhibit 2001, dated Dec. 10, 2018.
"Patent Owner's Preliminary Response," IPR2018-01549, Paper 8, dated Nov. 29, 2018.
"Patent Owner's Preliminary Response," IPR2018-01658, Paper 6, dated Dec. 11, 2018.
"Petition For Inter Partes Review of U.S. Pat. No. 9,089,362 Under 35 U.S.C. § 312 and 37 C.F.R. § 42.104," *Cardiovascular Systems, Inc.* v. *Cardio Flow, Inc.*, IPR2018-01658, Paper 1, dated Sep. 5, 2018.
"Petition For Inter Partes Review of U.S. Pat. No. 9,788,853 Under 35 U.S.C. § 312 and 37 C.F.R. § 42.104," *Cardiovascular Systems, Inc.* v. *Cardio Flow, Inc.*, IPR2018-01549, Paper 1, dated Aug. 17, 2018.
Declaration of Aleksey Filippov, Apr. 23, 2007, 1 page.
Declaration of Dmitri Prudnikov, Apr. 23, 2007, 1 page.
Excerpt from Deposition of Dmitri Prudnikov, Mar. 5, 2008, 7 pages.
Excerpt from Deposition of Dmitri Prudnikov, Mar. 6, 2008, 54 pages.
Exhibits Nos. 14, 31 & 32, from Deposition of Dmitri Prudnikov, Mar. 5, 2008, 3 pages.
Exhibits Nos. 33-39 from Deposition of Dmitri Prudnikov, Mar. 6, 2008, 47 pages.
Extended European Search Report in European Appln No. 15737946.2, dated Aug. 1, 2017, 8 pages.
Extended European Search Report in European Appln No. 18758512.0, dated Jan. 20, 2020, 7 pages.
International Preliminary Report on Patentability in International Appln. No. PCT/EP2010/054548, mailed on Oct. 4, 2011, 8 pages.
International Preliminary Report on Patentability in International Appln. No. PCT/EP2010/054550, mailed on Oct. 4, 2011, 7 pages.
International Preliminary Report on Patentability in International Appln. No. PCT/US2015/011212, mailed on Jul. 19, 2016, 8 pages.
International Search Report and Written Opinion in International Application No. PCT/EP2007/056499, mailed on Nov. 5, 2007, 3 pages.
International Search Report and Written Opinion in International Application No. PCT/EP2007/056500, mailed on Dec. 11, 2007, 6 pages.

(56) References Cited

OTHER PUBLICATIONS

International Search Report and Written Opinion in International Application No. PCT/EP2007/056516, mailed on Oct. 17, 2007, 3 pages.
International Search Report and Written Opinion in International Application No. PCT/EP2007/062777, mailed on Apr. 9, 2008, 2 pages.
International Search Report and Written Opinion in International Application No. PCT/EP2008/065986, mailed on Feb. 26, 2009, 3 pages.
International Search Report and Written Opinion in International Application No. PCT/US2015/011212, mailed on May 6, 2015, 9 pages.
International Search Report and Written Opinion in International Application No. PCT/US2017/26179, mailed on Oct. 4, 2017, 11 pages.
International Search Report and Written Opinion in International Application No. PCT/US2018/019238, mailed on May 8, 2018, 16 pages.
Invitation To Pay Additional Fees And, Where Applicable, Protest Fee in Application No. PCT/US2017/26179, mailed on Jul. 6, 2017, 2 pages.
Yevzlin, et al., "ASDIN Original Investigations: How I Do It: Directional Atherectomy for In-Stent Restenosis of a PTFE Arteriovenous Graft," Seminars in Dialysis, 2008, 21(3):266-268.

\* cited by examiner

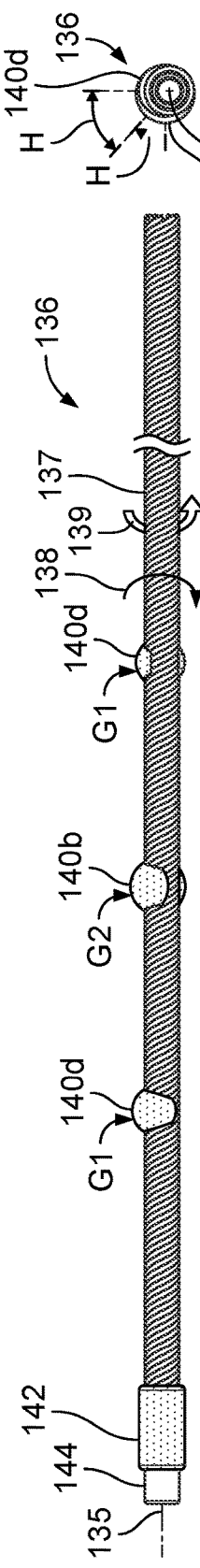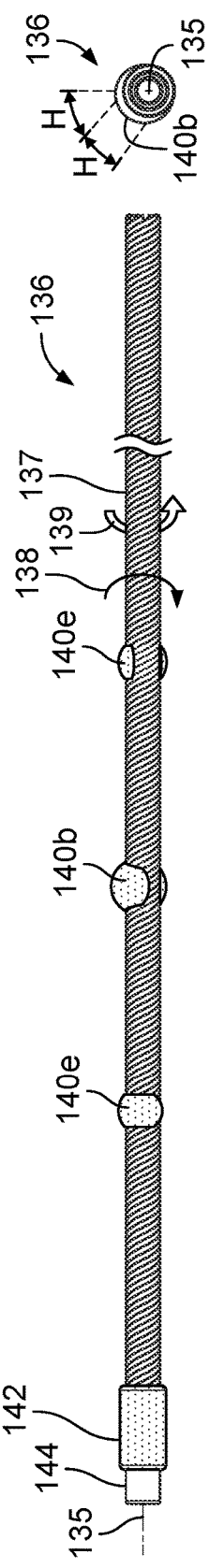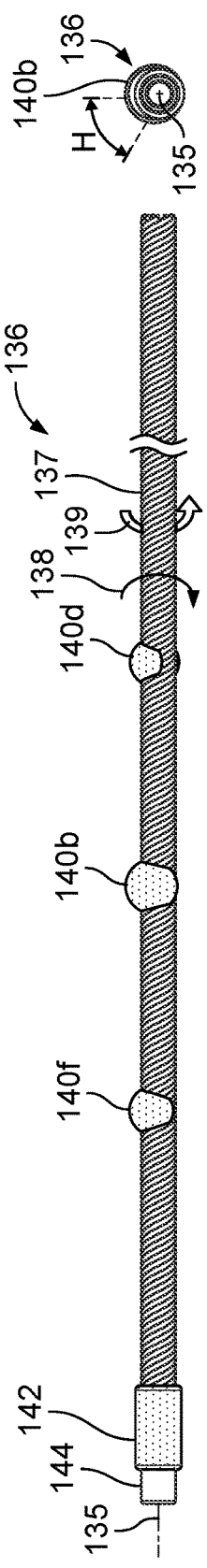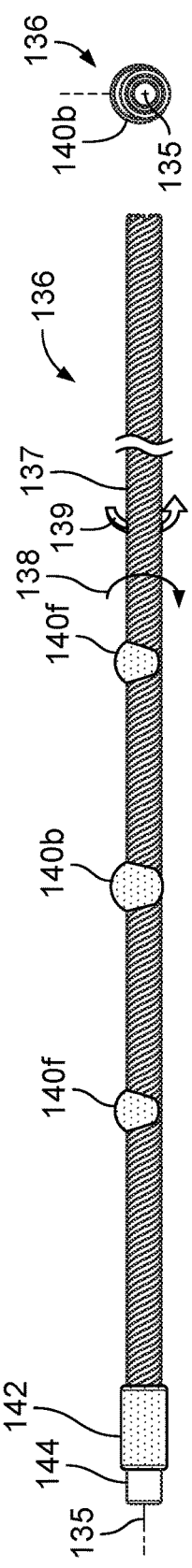

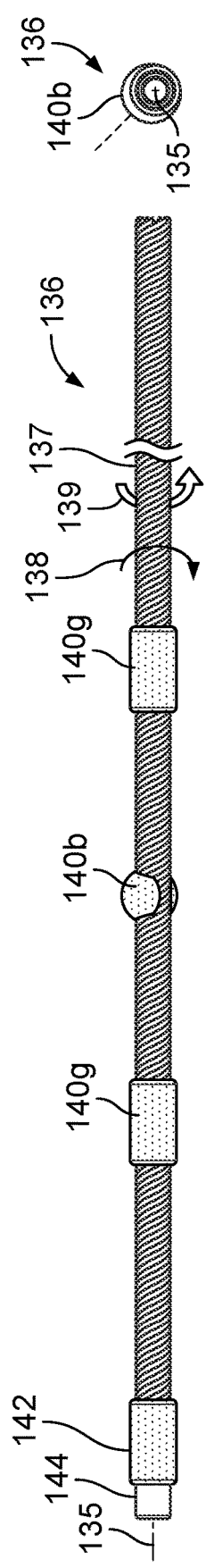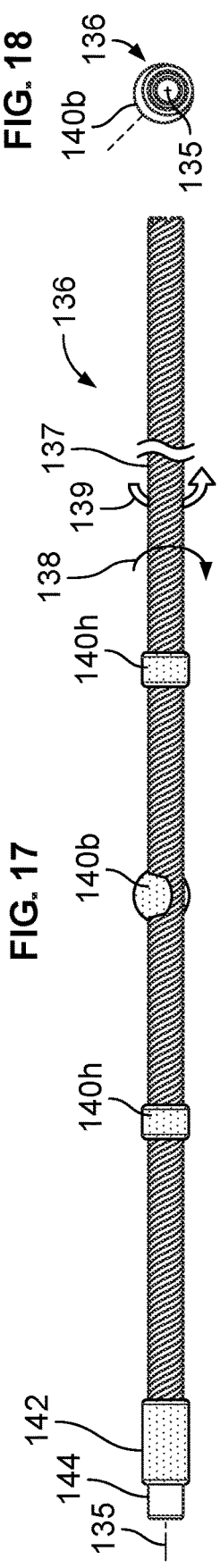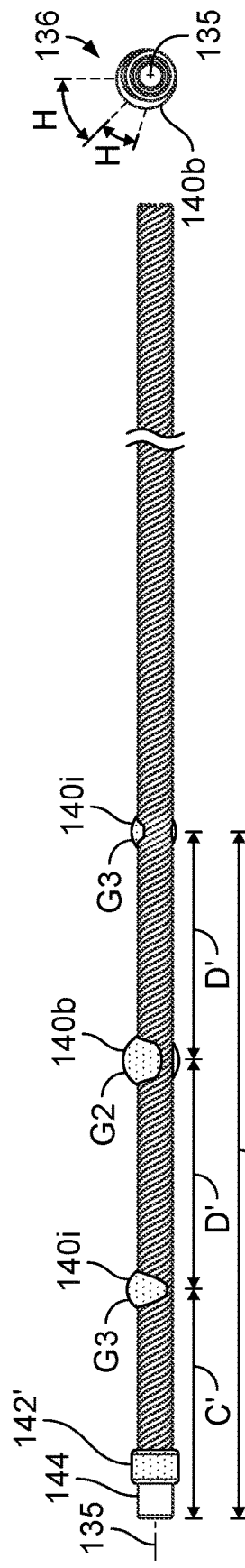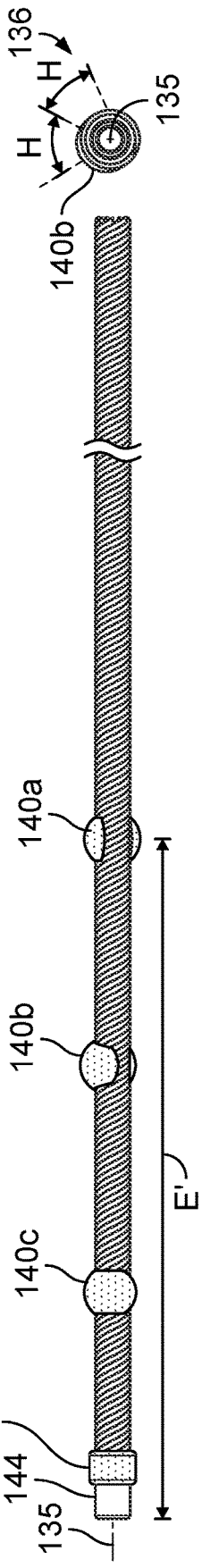

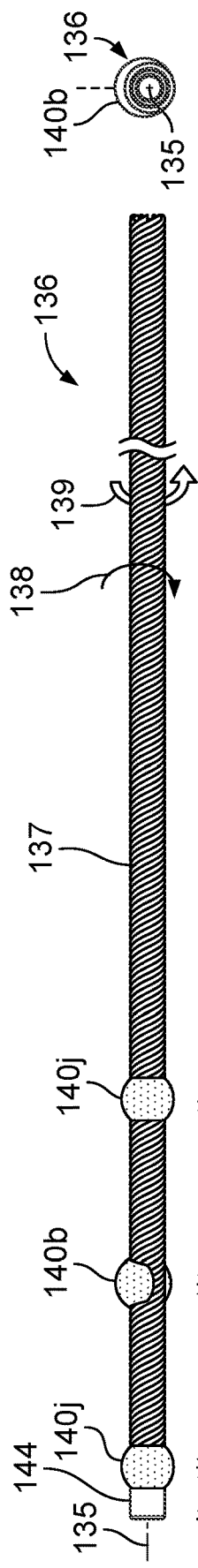

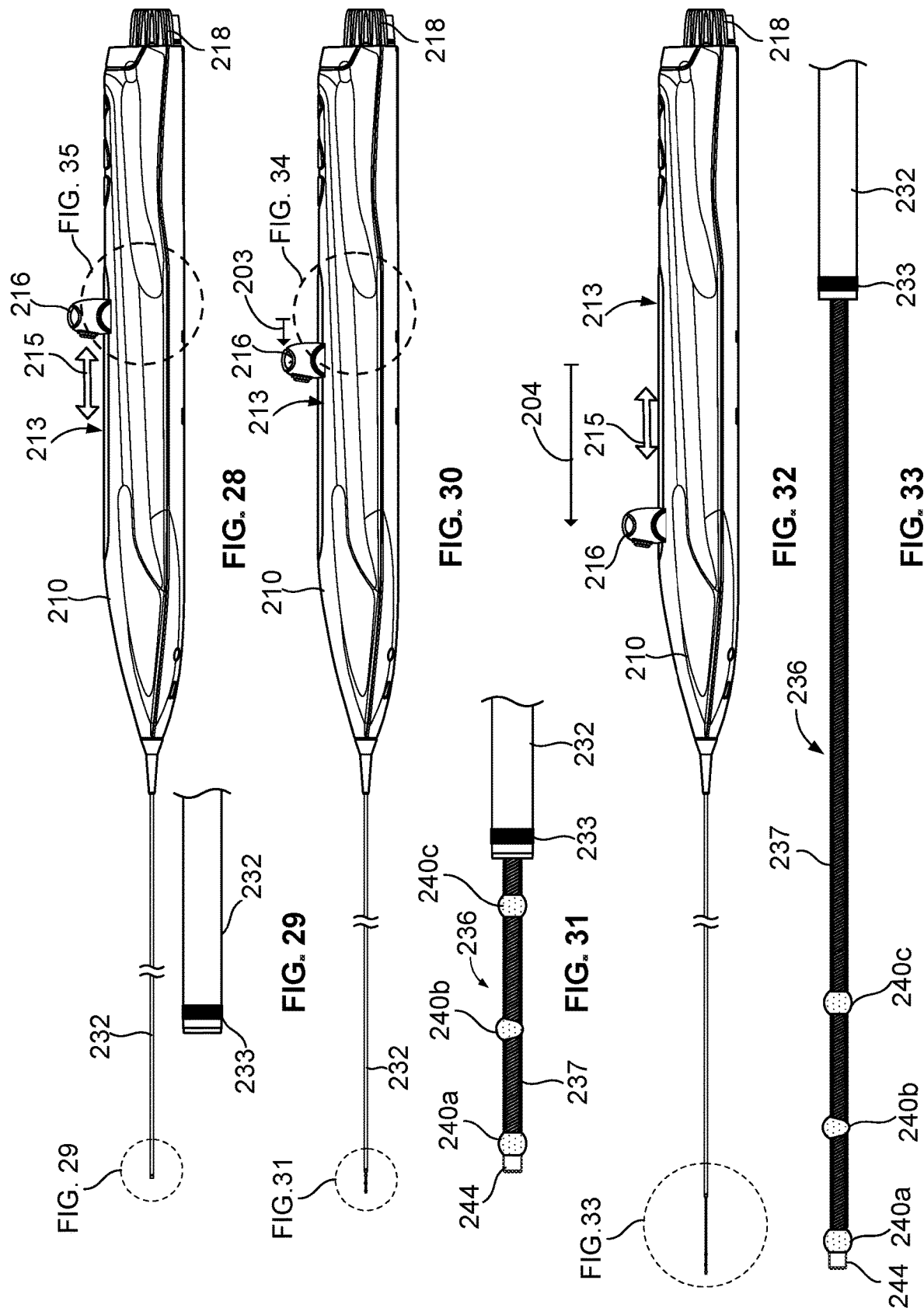

ROTATIONAL ATHERECTOMY DEVICES AND METHODS

CROSS-REFERENCE TO RELATED APPLICATIONS

This application claims priority under 35 U.S.C. § 119 to U.S. Provisional Application Ser. No. 63/542,438, filed on Oct. 4, 2023, and to U.S. Provisional Application Ser. No. 63/523,583, filed on Jun. 27, 2023, the contents of each of which are incorporated herein by reference in their entirety.

TECHNICAL FIELD

This document relates to rotational atherectomy devices and systems for removing or reducing stenotic lesions in blood vessels, for example, by urging one or more abrasive elements in an orbital motion within the vessel to remove (partially or completely) the stenotic lesion material.

BACKGROUND

Atherosclerosis, the clogging of arteries with plaque, is often a result of coronary heart disease or vascular problems in other regions of the body. Plaque can be formed from fat, cholesterol, calcium, and other substances found in the blood. Over time, the plaque hardens and narrows the arteries. This limits the flow of oxygen-rich blood to organs and other parts of the body.

Blood flow through the central and peripheral arteries (e.g., carotid, iliac, femoral, renal, etc.) can be similarly affected by the development of atherosclerotic blockages. For example, peripheral artery disease (PAD) can be serious because without adequate blood flow, the kidneys, legs, arms, and feet may suffer irreversible damage. Left untreated, the tissue may die or harbor infection. In another example, coronary artery disease (CAD) arises from the buildup of atherosclerotic material in one or more coronary arteries and may result in a deprivation of blood, oxygen, and nutrients to the heart muscle.

Rotational atherectomy can be used to treat such blockages in some types of blood vessels. In some versions of rotational atherectomy, a drive shaft carrying an abrasive burr or other abrasive surface (e.g., having diamond grit or diamond particles) rotates at a high speed within the vessel, and the clinician operator slowly advances the atherectomy device distally so that the abrasive burr scrapes against the occluding lesion and grinds it into very small particles, reducing the occlusion and improving blood flow through the vessel. While rotational atherectomy is commonly performed in larger arteries in the leg, such a process can be obstructed in small arteries, such as those below the ankle (e.g., in the feet) or in particular coronary arteries (e.g., in the left anterior descending coronary artery or the left circumflex coronary artery), especially where the vessel interior diameter is often 3 mm or less and the access path follows a tortuous route.

SUMMARY

Some embodiments of rotational atherectomy systems described herein can remove (partially or completely) stenotic lesions in blood vessels by rotating one or more abrasive elements in an orbital path to abrade and breakdown the lesion. In particular implementations, multiple abrasive elements are arranged along a distal portion of a drive shaft with an improved configuration/relative sizing so as to facilitate both efficient navigation into smaller blood vessels (below the ankle or in the heart) and effective orbital paths for abrading stenotic material in such smaller vessels. Additionally, some versions of the improved configuration of the multiple abrasive elements are arranged along the drive shaft can be effective for the removal or reduction of stenotic lesions in larger vessels too (e.g., those in the leg above the ankle or larger coronary arteries), thereby providing the user with options for efficiently treating a variety of arterial sites during a single procedure.

In one aspect, this disclosure is directed to a rotational atherectomy device for removing stenotic lesion material from a pedal artery or coronary artery of a patient. The device can include an elongate flexible drive shaft defining a longitudinal axis and comprising a torque-transmitting coil of one or more filars that are helically wound around the longitudinal axis in a filar wind direction from a distal end to a proximal end. The device may also include one or more abrasive burrs (e.g., such as a series of abrasive burrs as illustrated herein below) fixedly mounted to a distal end portion of the torque-transmitting coil. Optionally, the abrasive burrs can have a maximum burr diameter of no greater than 1.25 mm. At least one of the abrasive burrs can be an eccentric abrasive burr having a center of mass offset from the longitudinal axis so as to orbit in a rotational direction opposite of the filar wind direction.

In another aspect, this disclosure describes a method for rotational atherectomy in a pedal artery below an ankle. The method can include advancing a torque-transmitting coil of a rotation atherectomy device over a guidewire and into a pedal artery below an ankle so that at least one abrasive burr mounted to a distal end portion of the torque-transmitting coil is proximate to a stenotic lesion within the pedal artery. Additionally, the method can further include rotating the torque-transmitting coil of the rotation atherectomy device so that the at least one abrasive burr mounted to the torque-transmitting coil abrades the stenotic lesion within the pedal artery.

Another aspect set forth in this disclosure is a method for rotational atherectomy in a coronary branch artery of a heart. The method can include advancing a torque-transmitting coil of a rotation atherectomy device over a guidewire and into a coronary branch artery of a heart so that at least one abrasive burr mounted to a distal end portion of the torque-transmitting coil is proximate to a stenotic lesion within the coronary branch artery. The method may also include rotating the torque-transmitting coil of the rotation atherectomy device so that the at least one abrasive burr mounted to the torque-transmitting coil abrades the stenotic lesion within the coronary branch artery.

Further aspects set forth in this disclosure include at least one of a 4-French introducible rotational atherectomy device, a pedal loop navigable rotational atherectomy device, and a coronary branch navigable rotational atherectomy device (as detailed below).

In another aspect, this disclosure describes a rotational atherectomy system. The system can include a torque-transmitting coil of one or more filars that are helically wound around in a filar wind direction from a distal end to a proximal end to define a coil diameter and a drive shaft axis. The system can further include one or more abrasive burrs (e.g., such as a series of abrasive burrs as illustrated herein below) fixedly mounted to a distal end portion of the torque-transmitting coil. Optionally, each of the abrasive burrs can have an outer burr diameter such that a burr-to-coil diameter ratio for all abrasive burrs along the torque-transmitting coil is 1.3 to 1.7. The system may also include a rotational atherectomy handle assembly coupled to a proximal end of the torque-transmitting coil. Optionally, the rotational atherectomy handle assembly may house an electric motor configured to, responsive to user input at an actuator of the rotational atherectomy handle assembly, drive rotation of the abrasive burrs about the drive shaft axis in a rotational direction.

In yet another aspect, this disclosure is directed to a rotational atherectomy device for removing stenotic lesion material from an artery. The device can include an elongate flexible drive shaft defining a longitudinal axis and comprising a torque-transmitting coil of one or more filars that are helically wound around the longitudinal axis in a filar wind direction from a distal end to a proximal end. The device can also include a series of abrasive burrs fixedly mounted to a distal end portion of the torque-transmitting coil and having a maximum burr diameter of no greater than 1.25 mm. Optionally, an intermediate abrasive burr of the series of abrasive burrs is an eccentric abrasive burr having a center of mass offset from the longitudinal axis so as to orbit in a rotational direction opposite of the filar wind direction. The series of abrasive burrs can also include a proximal abrasive burr and a distal abrasive burr that each have a center of mass coaxial with the longitudinal axis.

Another aspect set forth in this disclosure is a rotational atherectomy system that includes a torque-transmitting coil, a series of abrasive burrs, and a rotational atherectomy handle assembly. The torque-transmitting coil can include one or more filars that are helically wound around in a filar wind direction from a distal end to a proximal end to define a coil diameter and a drive shaft axis. The series of abrasive burrs can be fixedly mounted to a distal end portion of the torque-transmitting coil and, optionally, may have a maximum burr diameter of no greater than 1.25 mm. The series of abrasive burrs can include a distal concentric abrasive burr, a proximal concentric abrasive burr, and an intermediate eccentric abrasive burr. Optionally, the distal concentric abrasive burr is coaxially mounted to a distal-most end of the torque-transmitting coil, the proximal concentric abrasive burr has the same size as the distal concentric abrasive burr and is coaxially mounted to the torque-transmitting coil at a position no greater than 0.5 inches from the distal-most end of the torque-transmitting coil, and the intermediate eccentric abrasive burr has a larger size than the distal and proximal concentric abrasive burrs and is mounted the torque-transmitting coil with a center of mass offset from the drive shaft axis. Additionally, the rotational atherectomy handle assembly can be coupled to a proximal end of the torque-transmitting coil and may house an electric motor configured to, responsive to user input at an actuator of the rotational atherectomy handle assembly, drive rotation of the series of abrasive burrs about the drive shaft axis in a rotational direction.

Some of the embodiments described herein may provide one or more of the following advantages. First, some embodiments of the rotational atherectomy system can be configured to provide a rotational atherectomy treatment in small arteries, such as those below the ankle (e.g., in the feet) or coronary arteries (e.g., in the left anterior descending coronary artery or the left circumflex coronary artery). In some examples described below, the orientation, relative spacing, and relative size of the abrasive elements along the distal end portion of the drive shaft (along with other features of the drive shaft) can collectively achieve an efficient access path to such small arteries, including those where the vessel interior diameter is often 3 mm or less and the access path follows a tortuous route.

Second, some embodiments of the rotational atherectomy devices and systems provided herein can advantageously advance through a relatively small percutaneous access point, such as an access point in a patient's upper leg having a small introducer sheath, and can having a sufficient balance of factors (e.g., length, maximum lateral radius from a central axis, flexibility, torque-transmission capabilities, etc.) to advance into the patient's foot or heart to remove (fully or partially) stenotic material from a targeted artery. In particular versions described below, the rotational atherectomy device can be in the form of a "4-French introducible" device, which as used herein means a rotational atherectomy device in which a maximum radius (measured from a central longitudinal axis of the torque-transmitting coil) among all of the torque-transmitting coil and the abrasive elements positioned thereon is smaller than the central access path of a 4-French introducer sheath, thereby providing slidable insertion through the 4-French introducer sheath.

Third, some embodiments of the rotational atherectomy devices and systems described herein a relative sizing ratio between a diameter of each abrasive element and a coil diameter of the drive shaft that is 1.7 or less. In particular examples described below, this relative sizing ratio is referred to as the burr-to-coil diameter ratio, and the burr-to-coil diameter ratio can be selected in accordance with the teachings herein in order to advantageously provide a drive shaft that can advance through a stenotic lesion in a small artery and then subsequently achieve an orbital path during rotation (e.g., an orbital path that is greater in size than a maximum stationary diameter of the abrasive elements) to abrade the stenotic lesion. In some implementations, the burr-to-coil diameter ratio can be about 1.3-1.7 for all abrasive elements along the torque-transmitting coil of the drive shaft. For example, the burr-to-coil diameter ratio can be 1.5-1.6 for a largest abrasive element mounted to the torque-transmitting coil and 1.3-1.4 for a smallest abrasive element mounted to the torque-transmitting coil. In a further example, the burr-to-coil diameter ratio can be 1.5-1.6 for each eccentric abrasive element mounted to the torque-transmitting coil and 1.3-1.4 for each concentric abrasive element mounted to the torque-transmitting coil.

Fourth, in some embodiments of the rotational atherectomy devices and systems that include multiple abrasive elements (at least one of which has a center of mass offset from the central axis of the drive shaft) that are longitudinally spaced apart for an advantageously condensed length of less than 5 cm from the distal-most tip of the drive shaft (preferably 2 cm or less from the distal-most tip of the drive shaft), with the combined radial angles of the all abrasive elements differing by less than 120 degrees (e.g., less than 90 degrees for the depicted embodiments herein) along that particular length of the drive shaft. Such a design can advantageously assist the eccentric abrasive elements to advance into tortuous arterial paths and small arteries and then (during rotation) achieve an orbit path that abrades targeted stenotic material from the arterial wall.

Fifth, some embodiments of the rotational atherectomy devices and systems provided herein can include an improved control handle that achieves simplified setup and convenient operation for a clinician. In particular examples, that the control handle can be a one-time-use, disposable unit that houses both and electric motor (for driving rotation of the drive shaft) and a fluid pump (for delivery of saline or another fluid toward the distal end of the drive shaft). Optionally, the controller for the handle (which includes a processor and memory storing the control instructions) can be housed is a separate, screenless housing (e.g., with the power adapter unit that plugs into an ordinary wall socket). In such optional implementations, the controller does not require a user interface screen and instead the user interface buttons are provided along the control handle that is connected to the controller via a detachable cable. Accordingly, in these optional implementations, the controller can be reusable over time with multiple control handles (all of which are one-time-use, disposable unit), thereby advantageously conserving costs while preserving the convenient disposability of the driveshaft shaft and handle.

Sixth, some embodiments of the rotational atherectomy devices and systems provided herein can be advantageously in the form of a "pedal loop navigable" device, which as used herein means a rotational atherectomy device in which the torque-transmitting coil provides flexibility during advancement through the tortuous path into a pedal loop of a foot below the ankle and the abrasive elements are oriented and sized to advance through a stenotic lesion within the foot for rotational atherectomy treatment in the foot.

Seventh, some embodiments of the rotational atherectomy devices and systems provided herein can be advantageously in the form of a "coronary branch navigable" device, which as used herein means a rotational atherectomy device in which the torque-transmitting coil provides flexibility during advancement through the tortuous path into a branch coronary artery (e.g., the left anterior descending coronary artery or the left circumflex coronary artery) of a heart and the abrasive elements are oriented and size to advance through a stenotic lesion within the branch coronary artery for rotational atherectomy treatment in the heart.

Eighth, some embodiments of the rotational atherectomy devices and systems provided herein can include an improved handle and sheath that facilitates retraction and extension of the abrasive elements to and from the sheath. The retraction of the abrasive elements within the sheath advantageously covers the abrasive burrs while the rotational atherectomy device is navigated to small arteries, such as those below the ankle (e.g., in the feet) or coronary arteries (e.g., in the left anterior descending coronary artery or the left circumflex coronary artery). The atherectomy device can be advantageously advanced to the target area while the abrasive surfaces of the abrasive elements are shielded from the vessel walls, thereby reducing the likelihood of scraping or engaging unintended regions of a bodily vessel along the navigation path. Instead, the atherectomy device is configured to smoothly navigate through the complex anatomy (e.g., especially along smaller arterial paths) while the abrasive elements are in a retracted position within a distal end of the sheath lumen, and then to adjust the abrasive elements distally from the sheath lumen after navigating to the targeted site (e.g., for rotational atherectomy treatment).

Ninth, some embodiments of the rotational atherectomy devices and systems provided herein can facilitate improved safety and ease of operation of the rotational atherectomy device. For example, the system can be configured to automatically prevent rotation of the drive shaft (and the abrasive elements thereon) when the abrasive elements are in a first longitudinal position (e.g., retracted within the sheath lumen) and to provide selective activation of rotation of the drive shaft when the abrasive elements are in a second longitudinal position (e.g., adjusted to extend distally from the sheath).

Accordingly, the system can provide an added safety control that facilitates improved and intuitive operation for a user both during navigation of the drive shaft (when the abrasive elements are positioned within a sheath) and during rotational atherectomy treatment after reaching the targeted site (permitting user-controlled rotation of the abrasive elements after the abrasive elements are extended from the sheath).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8 is a longitudinal side view of an alternative embodiment of a distal portion of a rotational atherectomy device, in accordance with some embodiments.

FIG. 9 is a distal end view of the rotational atherectomy device of FIG. 8.

FIG. 10 is a longitudinal side view of an alternative embodiment of a distal portion of a rotational atherectomy device, in accordance with some embodiments.

FIG. 11 is a distal end view of the rotational atherectomy device of FIG. 10.

FIG. 12 is a longitudinal side view of an alternative embodiment of a distal portion of a rotational atherectomy device, in accordance with some embodiments.

FIG. 13 is a distal end view of the rotational atherectomy device of FIG. 12.

FIG. 14 is a longitudinal side view of an alternative embodiment of a distal portion of a rotational atherectomy device, in accordance with some embodiments.

FIG. 15 is a distal end view of the rotational atherectomy device of FIG. 14.

FIG. 17 is a longitudinal side view of an alternative embodiment of a distal portion of a rotational atherectomy device, in accordance with some embodiments.

FIG. 18 is a distal end view of the rotational atherectomy device of FIG. 17.

FIG. 19 is a longitudinal side view of an alternative embodiment of a distal portion of a rotational atherectomy device, in accordance with some embodiments.

FIG. 20 is a distal end view of the rotational atherectomy device of FIG. 19.

FIG. 21 is a longitudinal side view of an alternative embodiment of a distal portion of a rotational atherectomy device, in accordance with some embodiments.

FIG. 22 is a distal end view of the rotational atherectomy device of FIG. 21.

FIG. 23 is a longitudinal side view of an alternative embodiment of a distal portion of a rotational atherectomy device, in accordance with some embodiments.

FIG. 24 is a distal end view of the rotational atherectomy device of FIG. 23.

FIG. 25 is a longitudinal side view of an alternative embodiment of a distal portion of a rotational atherectomy device, in accordance with some embodiments.

FIG. 26 is a distal end view of the rotational atherectomy device of FIG. 25.

FIG. 28 is a longitudinal side view of the rotational atherectomy system of FIG. 27 with the rotational atherectomy device in an exemplary proximal position, in accordance with some embodiments.

FIG. 29 is a longitudinal side view of a distal end of the rotational atherectomy system and rotational atherectomy device of FIG. 28.

FIG. 30 is a longitudinal side view of the rotational atherectomy system of FIG. 27 with the rotational atherectomy device in an exemplary proximal operating position, in accordance with some embodiments.

FIG. 31 is a longitudinal side view of a distal end of the rotational atherectomy system and rotational atherectomy device of FIG. 30.

FIG. 32 is a longitudinal side view of the rotational atherectomy system of FIG. 27 with the rotational atherectomy device in an exemplary distal operating position, in accordance with some embodiments.

FIG. 33 is a longitudinal side view of a distal end of the rotational atherectomy system and rotational atherectomy device of FIG. 32.

Like reference symbols in the various drawings indicate like elements.

DETAILED DESCRIPTION OF ILLUSTRATIVE EMBODIMENTS

Figure 1:
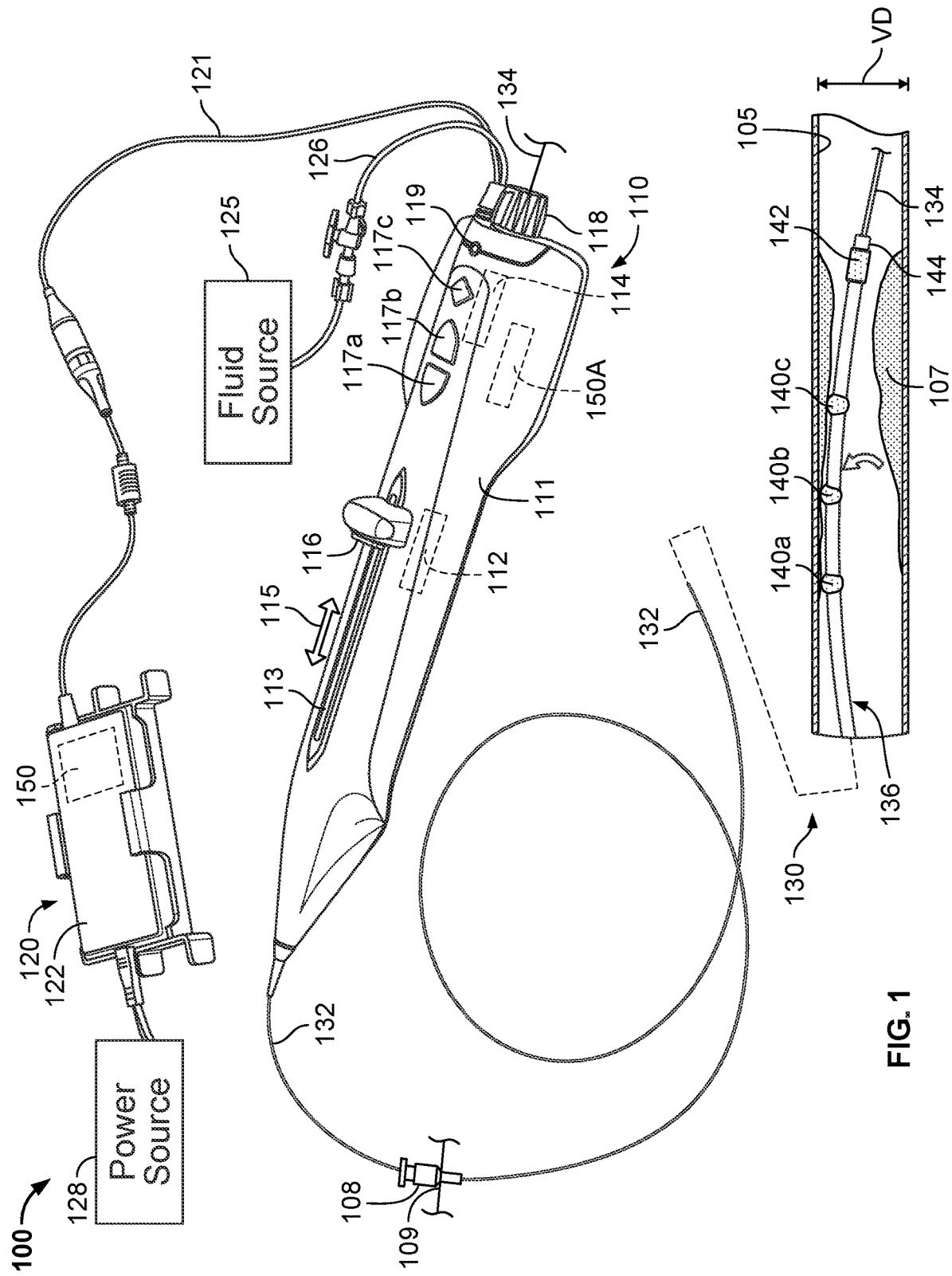
FIG. 1 a perspective view of an example rotational atherectomy system, in accordance with some embodiments.

Referring to FIG. 1, in some embodiments a rotational atherectomy system 100 for removing (partially or completely) a stenotic lesion 107 from a targeted blood vessel 105 can include an actuator handle assembly 110 that controls movement of an elongate flexible drive shaft assembly 130. The drive shaft assembly 130 includes a flexible drive shaft 136, and a distal end portion of the driveshaft 136 includes one or more abrasive elements 140a-c configured to abrade the stenotic lesion 107 in the targeted vessel 105. As described in more detail below, the abrasive elements 140a-c can have a selected configuration and relative sizing along the distal end portion of the drive shaft 136 so as to improve navigation into smaller blood vessels below the ankle or in the heart while also achieving an effective orbital path for abrading the stenotic material 107 in those vessels. (In the depicted example, the targeted blood vessel 105 has a vessel diameter VD of 3 mm or less, and about 2.5 mm as shown, while the initial path through the stenotic lesion is significantly smaller than that.) Optionally, the abrasive elements 140 and drive shaft 136 can have a selected configuration and relative sizing (e.g., FIGS. 2-3, 8-15, and 17-26) that advantageously provides advancement through a small percutaneous introducer 108 (e.g., sized to slidably receive instruments of 4-French diameter or smaller) at a percutaneous opening 109 in a patient's leg, and can further navigate through a stenotic lesion 107 in a small artery 105, such as those below the ankle (e.g., in the feet) or coronary arteries (e.g., in the left anterior descending coronary artery or the left circumflex coronary artery) prior to sweeping a larger orbital path (during rotation of the driveshaft 136) for abrading the stenotic material 107.

The system 100 can also include a power adapter 120 and a fluid source 125 (e.g., a saline bag) connectable to the actuator handle assembly 110, and the actuator handle assembly 110 can house therein an electric motor 112 (configured to drive rotation of the driveshaft 136) and fluid pump 114 (configured to urge a fluid such as saline toward the distal end portion of the driveshaft 136. As described in more detail below, a controller 150 for activating the electric motor 112 and the pump 114 (responsive to inputs at the user interface buttons 116 and 117a-c of the handle assembly 110) can be contained inside a housing 122 of the power adapter 120 so that it is reusable with subsequent handle assemblies after the first handle assembly 110 is discarded (a single-use handle assembly). Alternatively, a controller 150A for operating the electric motor 112 and the pump 114 can be contained within the housing in the handle assembly 110 (in proximity to the electric motor 112 and the pump 114), and the entire handle assembly 110 can be discarded after a single use with a patient. In both options, the handle assembly 110 can be operated by a clinician using a simplified, screenless interface to perform and control the rotational atherectomy procedure (e.g., without a graphic display screen along the handle assembly or on a separate unit connected to the handle assembly).

Still referring to FIG. 1, the elongate flexible drive shaft assembly 130 includes a sheath 132 that extends over a majority length of the flexible drive shaft 136 such that the abrasive elements 140a-c on the distal end portion of the drive shaft 136 are positioned distally of a distal-most end of the sheath 132. A proximal end of the sheath 132 is fixed to a distal end of the handle assembly 110. The flexible drive shaft 136 is slidably and rotatably disposed within a lumen of the sheath 132. The flexible drive shaft 136 defines a longitudinal lumen in which a guidewire 134 is slidably disposed. The guidewire 134 can extend through the handle assembly 110, the sheath 132, and the drive shaft 136 such that a proximal end of the guidewire 134 protrudes proximally from a rear port of a guidewire brake 118 at a proximal end of the handle assembly 110 while a distal end of the guidewire 134 extends distally of a distal-most end of the drive shaft 136. In this embodiment, the flexible drive shaft 136 includes a torque-transmitting coil of one or more helically wound filars that defines the longitudinal lumen along a central longitudinal axis. The drive shaft 136 is configured to rotate about the longitudinal axis while the sheath 132 remains generally stationary. Hence, during a rotational atherectomy procedure, the sheath 132 and the guidewire 134 are generally stationary while the flexible drive shaft 136 is controllably moved (e.g., rotating about the longitudinal axis and periodically longitudinally translating proximally and/or distally).

Figure 6:
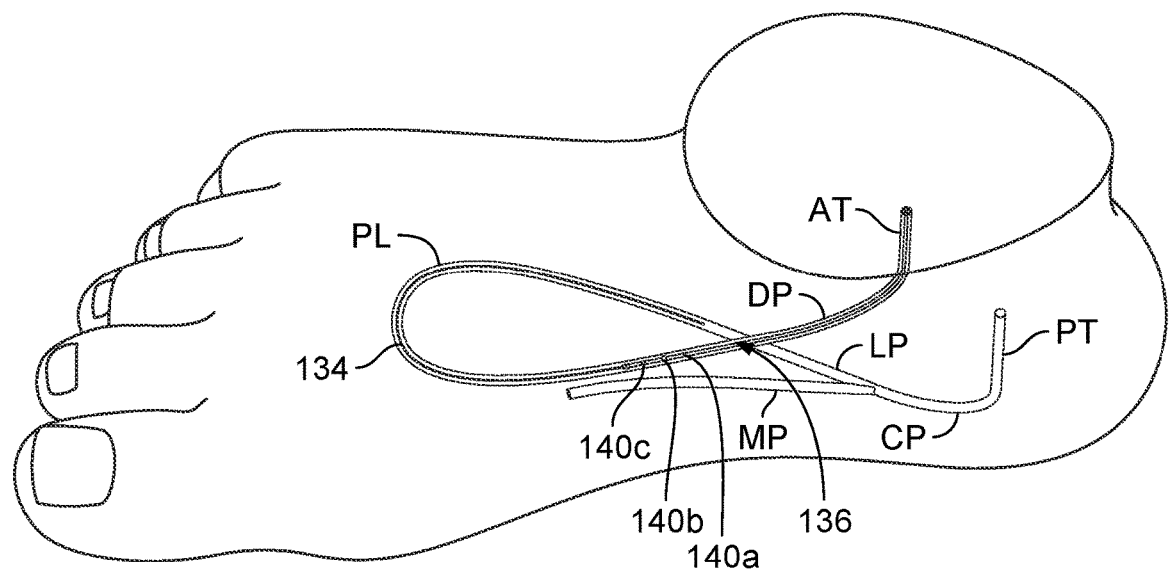
FIG. 6 is a perspective view of the distal portion of the example rotational atherectomy system of FIG. 1 in a pedal blood vessel below an ankle, in accordance with some embodiments.

In the depicted embodiment, the exposed distal end portion of the driveshaft 136 includes one or more abrasive elements 140a-c, a (optional) distal stability element 142, and a (optional) concentric tip member 144 (refer to FIG. 6). In the depicted embodiment, the one or more abrasive elements includes a set of three eccentric abrasive elements 140a-c that are fixedly mounted to an exterior of the torque-transmitting coil of the driveshaft 136 such that a center of massive for each abrasive element 140a-c is offset from a central longitudinal axis of the torque-transmitting coil. In this embodiment, the distal stability element 142 is concentrically-fixed to an exterior of the torque-transmitting coil of the driveshaft 136 between a distal-most one of the eccentric abrasive elements 140a-c and the concentric tip member 144. As such, the center of mass of the distal stability element 142 is aligned with the central axis of the drive shaft 136 while the center of mass of each abrasive element 140a-c is offset from the central axis of the drive shaft 136. The concentric tip member 144 (refer to FIG. 6) is affixed to, and extends distally from, the terminal distal-most end of the torque-transmitting coil. As described in more detail below, the concentric tip member 144 has a smoother surface than the abrasive surfaces of the distal stability element 142 and the eccentric abrasive elements 140a-c, and the concentric tip member 144 can be configured to provide initial penetration (and, optionally, dilation) through the stenotic lesion 107 in the targeted vessel 105.

Still referring to FIG. 1, as the drive shaft 136 is rotated about its longitudinal axis, the eccentric abrasive elements 140a-c (and the portion of the drive shaft 136 to which the one or more abrasive elements 140a-c are affixed) will be urged in an orbit path relative to the central axis of the drive shaft 136 (also as described below, for example, in connection with FIG. 5). In general, faster speeds (rpm) of rotation of the drive shaft 136 will result in larger diameters of the orbit (within the limits of the vessel diameter). The orbiting one or more abrasive elements 140a-c will contact the stenotic lesion 107 to abrade the lesion to a reduced size with each traversal path through the lesion 107 (i.e., small particles of the lesion will be abraded from the lesion). Depending upon the rotation speed and the surrounding environment within the vessel 105, the rotating distal stability element 142 can remain generally closer to or at the longitudinal axis of the drive shaft 136 during the rotational atherectomy procedure. In some optional embodiments, two or more distal stability elements 140 are included. As described further below, contemporaneous with the rotation of the drive shaft 136, the drive shaft 136 can be translated back and forth (distally and proximally) along the longitudinal axis of the drive shaft 136. Hence, the stenotic lesion 107 can be abraded radially and longitudinally by virtue of the simultaneous translation and orbital rotation of the abrasive elements 140a-c.

Additionally, the torque-transmitting coil of the flexible drive shaft 136 is laterally flexible so that the drive shaft 136 can readily advance through a tortuous arterial path (e.g., in the pedal loop or in a coronary branch artery), and so that a portion of the drive shaft 136 at, and adjacent to, the one or more abrasive elements 140 can laterally deflect when acted on by the centrifugal forces resulting from the rotation of the one or more eccentric abrasive elements 140. In the depicted embodiment, the drive shaft 136 comprises one or more helically wound wires (or filars) that provides a uniform coil diameter than is less than the diameters of all of the abrasive elements 140a-c and the distal stability element 142. As described in more detail below, this relative sizing is referred to as the burr-to-coil diameter ratio, and the burr-to-coil diameter ratio can be about 1.3-1.7 for all abrasive burrs (elements 140a-c and distal stability element 142) along the torque-transmitting coil of the drive shaft. As such, the torque-transmitting coil of the flexible drive shaft 136 can achieve both sufficient lateral flexibility during navigation through a tortuous path (e.g., in a patient's foot or heart) and sufficient longitudinal rigidity to be pushed through a stenotic lesion (while transmitting torque to rotate the abrasive elements 140a-c) in a small artery. In some embodiments, the one or more helically wound wires (filars) of the torque-transmitting coil of the flexible drive shaft 136 comprise a metallic material such as, but not limited to, stainless steel (e.g., 316, 316L, or 316LVM), nitinol, titanium, titanium alloys (e.g., titanium beta 3), carbon steel, or another suitable metal or metal alloy. Any suitable number of individual filars can be included to construct the drive shaft 136. For example, in some embodiments one, two, three, four, five, six, seven, eight, nine, ten, eleven, twelve, thirteen, fourteen, fifteen, or more than fifteen individual filars can be helically wound among each other to make up the drive shaft 136. As described further below, the direction in which the filars of the drive shaft 136 are wound is a design feature that can be selected to obtain desirable, advantageous operational characteristics. For example, the drive shaft 136 can be formed using one or more filars that are wound about the shaft's central axis in a wind direction that is opposite from the rotational direction of the drive shaft 136 urged by the handle assembly 110, which can provide a number of benefits and improved safety during use of the drive shaft 136 with the guidewire 134 in small-sized arteries below the ankle or in the heart.

Still referring to FIG. 1, the torque-transmitting coil of the drive shaft 136 in this embodiment defines a hollow central core (e.g., referred to as a central lumen of the drive shaft 136), which can slidably receive the guidewire 134 therein. In some embodiments, the lumen can be used to aspirate particulate or to convey fluids that are beneficial for the atherectomy procedure. In use, the guidewire 134 is advanced to the targeted vessel 105, and then the drive shaft 136 is advanced over the guidewire 134 in order to reach the targeted vessel 105. The guidewire 134 has a length sufficient to extend through the entire drive shaft 136 and the entire handle assembly 110. As such, a proximal end of the guidewire 134 protrudes proximally from the rear port of the guidewire brake 118 at a proximal end of the handle assembly 110 while a distal end of the guidewire 134 extends distally of a distal-most end of the drive shaft 136.

In the depicted embodiment, the concentric tip member 144 is welded or otherwise fixed to a distal-most end of the torque-transmitting coil of the drive shaft 136 (e.g., axially distal of the coil), and the distal stability element 142 is welded or otherwise fixed to the distal-most end of the torque-transmitting coil of the drive shaft 136 (e.g., radially outward of the coil). As described in more detail below, the smooth initial surface of the concentric tip member 144 followed by the abrasive surface on the distal stability element 142 can help facilitate the initial expansion and abrasion of a pilot path through the stenotic lesion 107 in the targeted vessel 105.

Still referring to FIG. 1, the one or more abrasive elements 140a-c (each of which may also be referred to as an abrasive burr) can comprise a biocompatible material that is coated with an abrasive media such as diamond grit, diamond particles, silicon carbide, and the like. In the depicted embodiment, the abrasive elements 140a-c includes a total of three discrete abrasive spheres/cylinders that are spaced apart from each other (and spaced relative to the distal stability element 142) to facilitate both navigation to, and orbital abrading within, a targeted small artery, including those where the vessel interior diameter is often 3 mm or less and the access path follows a tortuous route. In the depicted embodiment, all three of abrasive elements 140a-c are spheres having the same diameter and are mounted in an eccentric spiral arrangement (described below in connection with FIGS. 2-3). Other embodiments depicted herein (e.g., refer to FIGS. 9-24) can also be used in accordance with the system of 100 of FIG. 1 to facilitate both navigation to, and orbital abrading within, a targeted small artery, including those where the vessel interior diameter is often 3 mm or less and the access path follows a tortuous route. As with the distal stability element 142, the abrasive burrs 140a-c may be mounted to the exterior of the torque-transmitting coil of the drive shaft 136 using a biocompatible adhesive, high temperature solder, welding, press fitting, and the like. Alternatively, the one or more abrasive elements 140a-c can be integrally formed as a unitary structure with the filars of the drive shaft 136 (e.g., using filars that are wound in a different pattern to create an axially offset structure, or the like).

Still referring to FIG. 1, the rotational atherectomy system 100 also includes the actuator handle assembly 110. The actuator handle assembly 110 includes a housing 111 and an internal carriage assembly (not shown) that translates along an actuator slot 113. For example, a user can grasp the actuator 116 to urge movement along the actuator slot 113, which causes the internal carriage assembly to slidably translate along the longitudinal axis of the handle assembly 110, as indicated by the arrow 115. In some embodiments the carriage assembly can be translated, without limitation, about 8 cm to about 12 cm, or about 6 cm to about 10 cm, or about 4 cm to about 8 cm, or about 6 cm to about 14 cm. As the carriage assembly is translated in relation to the housing 111, the drive shaft 136 translates in relation to the sheath 132 in a corresponding manner. As such, the user can reciprocate the distal end portion of the drive shaft 136 in distal and proximal directions relative to the stenotic lesion 107 within the targeted vessel 105.

The handle assembly 110 has a cable connection 121 with a power adapter 120 (configured to receive electrical power from a power source 128 such as a wall plug) and fluid line connection 126 with a saline source 125. The cable 121 can communicate both power and data (e.g., when the controller 150 is housed within the power adapter housing 122), or alternatively, can communicate electrical power (e.g., when implementing the version with the controller 150A that is housed in the handle housing 111). The cable 121 includes a removable connection jack so that the handle assembly 110 can be readily discarded after a single use and the power adapter 120 can be reused with subsequent handle assemblies. The fluid line connection 126 can include a luer fitting and a flow on-off valve so that a user can removably connect the handle assembly to a pole-mounted saline bag or other fluid source 125 without the need for an external pump mechanism positioned exterior to the handle housing 111.

Still referring to FIG. 1, the actuator 116 of the handle assembly 110 includes a rotational power button that activates the electrical motor 112 (carried by the internal carriage assembly) to drive the rotation of the drive shaft 136. For example, when the rotational power button of the actuator 116 is depressed, power is supplied to the electric motor 112, which is coupled to the drive shaft 136 via a set of gears. It should be understood that the rotational atherectomy system 100 is configured to rotate the drive shaft 136 at a high speed of rotation (e.g., 20,000-160,000 rpm) such that the eccentric one or more abrasive elements 140a-c revolve in an orbital path to thereby contact and remove portions of a target lesion 107 (even those portions of the lesion that are spaced farther from the axis of the drive shaft 136 than the maximum radius of the abrasive elements 140a-c).

To operate the handle assembly 110 during a rotational atherectomy procedure, a clinician can grasp the actuator 116 and depress rotational power button (on the actuator 116) with the same hand. The clinician can move (translate) the actuator 116 along the slot 113 distally and proximally by hand (e.g., back and forth in relation to the housing 111), while maintaining the rotational power button of the actuator 116 in the depressed state. In that manner, a target lesion 107 can be abraded radially and longitudinally by virtue of the resulting orbital rotation and translation of the abrasive elements 140a-c.

To further operate the handle assembly 110 during a rotational atherectomy procedure, a clinician can select a rotational speed using electrical switches 117a and 117b. In some cases, the rotational speed can be selected through a set of predefined speeds (e.g., at least two predefined speed settings, such as "low" and "high") with electrical switch 117a causing an increase in the speed setting and electrical switch 117b causing a decrease in the speed setting. Optionally, each of the electrical switches 117a-b can also include a light indicator. For example, when the electrical switches 117a-b allow for selection for a "high" and "low" speed, respectively, the electrical switches 117a-b can each have a single light, such that when a speed is selected, the light corresponding to the selected electrical switch 117a or 117b is illuminated to inform a clinician of the selected speed. In some embodiments, the light can shine through electrical switches 117 and 117b. Alternatively, a light can be positioned proximal electrical switch 117a-b. As another example, when the electrical switches 117a-b allow modification of a speed between a range of speeds, the light indicator can be a light bar, such that a number of lights illuminated on the light bar correspond to a selected speed.

Still referring to FIG. 1, handle assembly 110 can include a fluid pump switch 117c, which can activate the internal fluid pump 114 to draw fluid (e.g., saline in this embodiment) from the fluid line 126 and urge the fluid through the sheath 132 toward the distal end portion of the drive shaft 136. As such, the fluid pump switch 117c can be used to both initially prime the sheath 132 (and remove air before insertion into the patient) and then selectively activate additional flush fluid through the sheath 132 and into the vessel 105. In some cases, a first depression of the fluid pump switch 117c will turn the internal pump 114 on, while a second depression will turn the pump 114 off. In some embodiments, the fluid pump switch 117c includes a light indicator, such that when the pump is on, a light is illuminated to inform the clinician that the pump is on.

In the depicted embodiment, the handle assembly 110 also includes a guidewire brake 118 that can be selectively actuated (e.g., pivoted relative to the handle housing 111 in this embodiment) to releasably clamp the guidewire 134 in a stationary position relative to the handle assembly 110 (and, in turn, stationary in relation to rotations of the drive shaft 136 during an atherectomy treatment). While the drive shaft 136 and handle assembly 110 are being advanced over the guidewire 134 to put the one or more abrasive elements 140 into a targeted position within a patient's vessel, the guidewire brake 118 is in a non-activated state (e.g., pivoted counter-clockwise about the central guidewire axis) from a rear perspective) so that the handle assembly 110 is free to slide in relation to the guidewire 134. Then, when the clinician is ready to begin the atherectomy treatment, the guidewire brake 118 can be activated (e.g., pivoted clockwise about the central guidewire axis) to mechanically engaged an exterior of the guidewire 134 and thereby releasably detain/lock the guidewire 134 in relation to the handle assembly 110. That way the guidewire 134 will not rotate while the drive shaft 136 is rotating, and the guidewire 134 will not translate while the actuator 116 is being manually translated in the direction 115.

Still referring to FIG. 1, handle assembly 110 can include a guidewire brake light 119 that positioned along an upper face of the handle housing 111 at a position proximal to the other user interface buttons 117a-c and adjacent to the guidewire brake 118. As such, a user can readily view the guidewire brake light 119 and receive confirmation of whether the guidewire brake 118 is fully activated (to clamp the guidewire 134) before selecting the rotational speed (e.g., buttons 117a-b) and activating rotation (e.g., button on the actuator 116). As such, the screenless user interface of the handle assembly 110 can provide a simplified and fluid hand motion for the user while also communicating effective information to the user. Optionally, the controller 150 (or 150A in other embodiments) can be configured to prevent the electric motor 112 from driving rotation of the drive shaft 136 until: (1) the guidewire brake 118 is activated (e.g., with the guidewire brake light 119 illuminated), (2) the pump 114 is activated to drive the flush fluid (e.g., via actuation of fluid pump switch 117c that then illuminates the button 117c), (3) a rotation speed has been selected via speed selection switches 117a and 117b (e.g., with a speed indicator light thereon being activated), or a combination of all these conditions. As another example, the indicator lights associated with the selection switches 117a and 117b, the fluid pump switch 117c, and the guidewire brake light 119 will alert a clinician that the rotational atherectomy system 100 should not be operated until all three systems (the motor, the pump, the guidewire brake) are activated. For example, each system may have a green light, such that three green lights indicates the clinician can proceed with the atherectomy procedure. Optionally, only the guidewire 118 needs to be actuated to allow rotation of the rotational atherectomy system 100.

Still referring to FIG. 1, the rotational atherectomy system 100 also includes the controller 150, which in this embodiment which includes a processor and computer-readable memory storing control instructions thereon. The controller 150 is configured to receive input from sensors housed within the handle assembly, to receive input from the user interface on the handle assembly 110 (e.g., switches/actuators 116, 117a-c, and 118), and to control the activation of the electric motor 112 and the pump 114 (responsive to inputs at the user interface switches/actuators). In this embodiment, the controller 150 is contained inside the housing 122 of the power adapter 120 so that it is reusable with subsequent handle assemblies after the first handle assembly 110 is discarded (e.g., after use with a first patient). As previously described, the cable 121 can provide data communication between the controller 150 and the components of the user interface (e.g., switches/actuators 116, 117a-c, and 118), the electric motor 112, the pump 114, and the feedback sensors housed within the handle assembly 110. In an alternative embodiment, the controller (including the processor and computer-readable memory storing the control instructions) can be provided in the form of controller 150A configured to be contained within the housing 111 of the handle assembly 110 (in proximity to the electric motor 112 and the pump 114). In both options, the handle assembly 110 can be operated by a clinician using the above-described simplified, screenless interface to perform and control the rotational atherectomy procedure (e.g., without a user interface display screen along the handle assembly or on the units connected to the handle assembly). Preferably, the controller 150 (or controller 150A) is housed in a manner that is sealed from fluids encountered by the handle assembly, such as saline, blood, or others.

Figure 2:
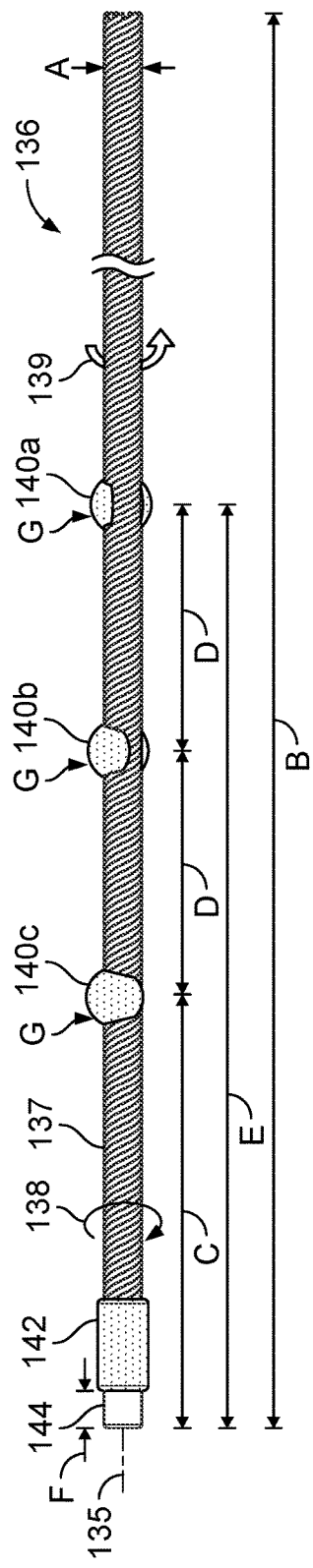
FIG. 2 is a longitudinal side view of a rotational atherectomy device of the system of FIG. 1.
Figure 3:
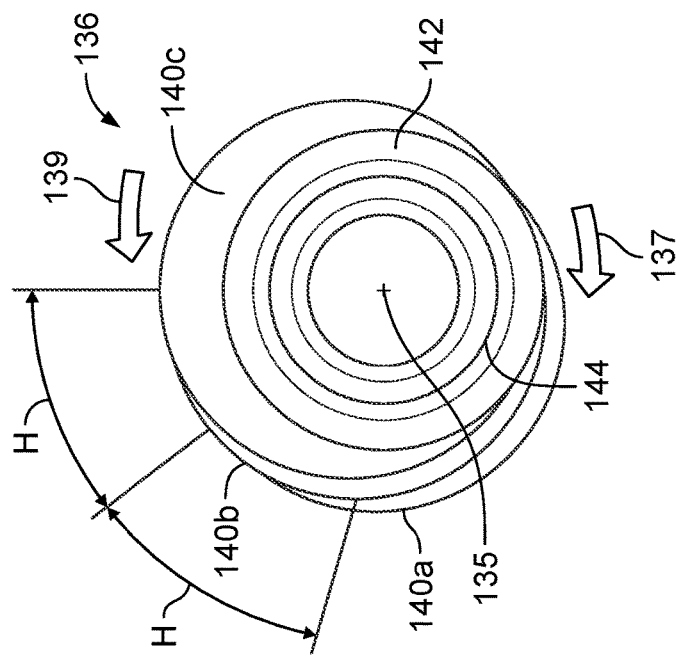
FIG. 3 is a distal end view of the rotational atherectomy device of FIG. 2.

Referring now to FIGS. 2-3, some embodiments of the distal end portion of the drive shaft 136 include an improved configuration of the abrasive burrs (and optionally the distal stability element) that provide a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the abrasive elements 140a-c are eccentrically-fixed to the torque-transmitting coil 137 of the driveshaft 136 while the distal stability element 142 (having a similar abrasive surface) is concentric with the torque-transmitting coil 137 of the drive shaft 136. As shown in FIG. 2, the torque-transmitting coil 137 as a coil diameter A, and all of the abrasive burrs 140a-c have the same diameter G (which is larger than the coil diameter). For example, the abrasive burrs 140a-c can have a diameter G of 1.0 mm to 1.33 mm, preferably 1.1 mm to 1.3 mm, and 1.25 mm in the depicted embodiment here (e.g., nominal diameter of 1.25 mm before application of thin abrasive coating). And, in such examples, the coil diameter A can be 0.7 mm to 0.9 mm, and preferably 0.8 mm in this depicted embodiment. Accordingly, some embodiments described herein a relative sizing ratio between the diameter G of each abrasive element 140a-c and the coil diameter A (e.g., a burr-to-coil diameter ratio) that is 1.7 or less. In some implementations, the burr-to-coil diameter ratio can be about 1.3-1.7 for all abrasive elements along the torque-transmitting coil of the drive shaft. In the depicted example, the burr-to-coil diameter ratio can be 1.5-1.6 for each eccentric abrasive element 140a-c mounted to the torque-transmitting coil 137 and 1.3-1.4 for the distal stability element 142 mounted to the torque-transmitting coil 137.

Also shown in FIG. 3, the centers of mass of the abrasive burrs 140a-c are offset in different planes at radial spacing angle H. For example, the radial spacing angle H of 5 degrees to 87.5 degrees, preferably 20 degrees to 60 degrees, and 37.5 degrees in the depicted embodiment here. As such, the combined radial angles of the all abrasive burrs 140a-c is less than 175 degrees (e.g., less than 120 degrees, and preferably less than 90 degrees in the depicted embodiment) along that particular length of the drive shaft carrying the abrasive burrs 140a-c.

Still referring to FIGS. 2-3, the abrasive burrs 140a-c can be mounted to the coil 137 so as to provide a compact end length E between the proximal-most abrasive element 140a and the distal-most tip of the drive shaft 136, which can be effective in treating stenotic lesions 107 in small arteries, such as those in the feet below the ankle or those in the coronary arteries. For example, the compact end length E can be 5 cm or less from the distal-most tip of the drive shaft 136, preferably 2 cm or less from the distal-most tip of the drive shaft 136, and about 1.9 cm (0.75 inches) in the depicted embodiment. Such an end length E can be relative compact compared to the overall length B of torque-transmitting coil 137. For example, the overall length B can be 150 cm to 250 cm, 110 cm to 200 cm, and about 197 cm (77.5 inches) in the depicted embodiment. As such, the end length E can be less than 1% of the overall length B. In some embodiments, the ratio of the overall length B to the end length E is greater than 50:1, about 90:1 to 140:1, and about 103:1 in the depicted embodiment. Also, in the depicted embodiment, the abrasive burrs 140a-c in the compact end length E includes a total of three discrete elements that are spaced apart from each other. In other embodiments, one, two, three, four, or five discrete abrasive elements are included in the set of abrasive elements within the compact end length E.

Additionally, within the compact end length E of the drive shaft 136, the relative spacing of the abrasive burrs 140a-c can advantageously affect the orbital path of the abrasive elements, the flexibility of the intermediate sections of the torque-transmitting coil (with such flexibility being useful during advancement through tortuous arterial paths), or both. For example, the distal-most abrasive burr 140c can be spaced from the distal-most end of the shaft by an extension length C, with the next abrasive burr 140b being spaced therefrom by a burr spacing distance D, and the proximal-most abrasive burr 140a being spaced apart therefrom by the same burr spacing distance D. In the depicted embodiment, the extension length C is greater than the burr spacing distance D, but they can be approximately equal in other embodiments (refer, for example, to FIGS. 21-24). For example, the extension length C can be 4 mm to 15 mm, 5 mm to 10 mm, and about 9 mm (0.35 inches) in the depicted embodiment, while the burr spacing distance D can be 2 mm to 7 mm, 4 mm to 6 mm, and about 5 mm (0.20 inches) in the depicted embodiment.

Still referring to FIGS. 2-3, some embodiments of the abrasive burrs 140a-c, the optional distal stability element 142, and the optional distal tip member 144 can provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery. The embodiment depicted in FIGS. 2-3 is provided in the form of a "4-French introducible" device, as described above.

Figure 4:
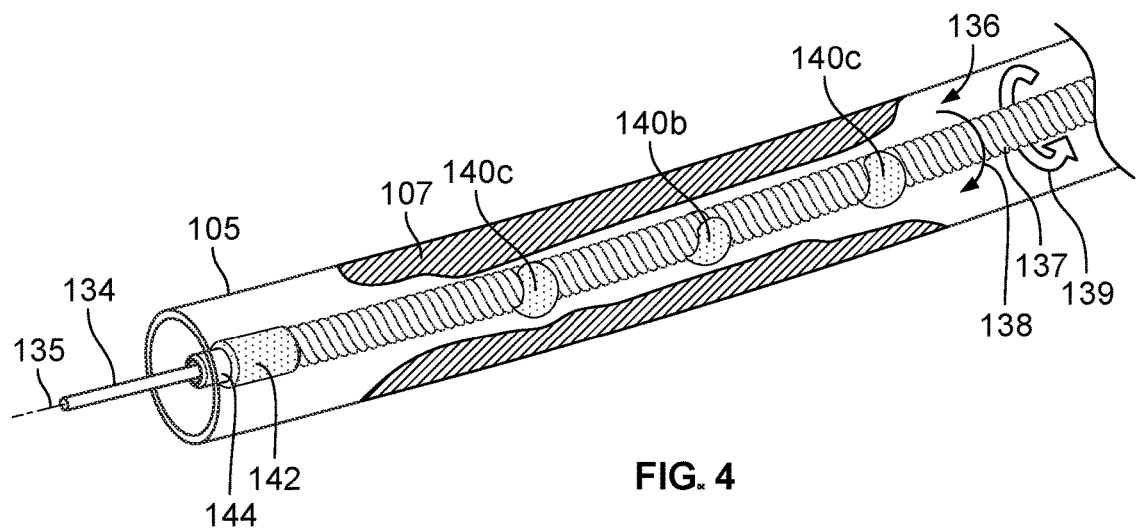
FIG. 4 is a perspective view of the distal portion of the example rotational atherectomy system of FIG. 1 in the blood vessel.

Referring now to FIG. 4, the filar wind direction 138 (e.g., the winding direction of filars of the torque transmitting coil 137 traversing from the distal end toward the proximal end) and the rotational direction 139 of the torque transmitting coil 137 (e.g., the rotational direction of the drive shaft 136 urged by the handle assembly 110) can be configured to provide a number of performance benefits during the rotational atherectomy in the pedal or coronary arteries, especially those where the vessel interior diameter is often 3 mm or less and the access path follows a tortuous route. For example, as shown in FIG. 4 (and also in FIGS. 2-3), the filar wind direction 138 is opposite from the rotational direction 139 of the torque transmitting coil 137, which can provide functional benefits when advancing into tight lesions in small arteries within the foot (below the ankle) or through a tortuous path into a branch coronary artery (e.g., the left anterior descending coronary artery or the left circumflex coronary artery). In particular, during rotation of the driveshaft 136 adjacent to such a lesion, one of the abrasive elements 140a-c, the distal stability element 142, or the distal tip 144 may catch on the bodily material or otherwise may be momentarily restrained from rotation (even though the proximal end of the drive shaft 136 is rotated by the handle assembly 110 (FIG. 1). In such circumstances, the filar wind direction 138 is opposite from the rotational direction 139 of the torque-transmitting coil 137 as shown in FIGS. 2-3, so the torque-transmitting coil 137 will not suffer a narrowed coil diameter that causes the torque-transmitting coil 137 to clamp down on the guidewire 134 (e.g., creating reduced flexibility and potentially other concerns in the narrow space with the vessel), but instead the coil diameter will remain the same or be momentarily expanded (safely avoiding a clamping effect on the guidewire 134).

Accordingly, the drive shaft 136 of the rotational atherectomy system 100 can have a configuration that provides safe and repeatable navigation into smaller blood vessels below the ankle or in the heart and effective orbital paths for abrading stenotic material in such smaller vessels. Such configurations can be particularly useful, for example, when implemented as a pedal loop navigable device, a coronary branch navigable device, or both.

Figure 5:
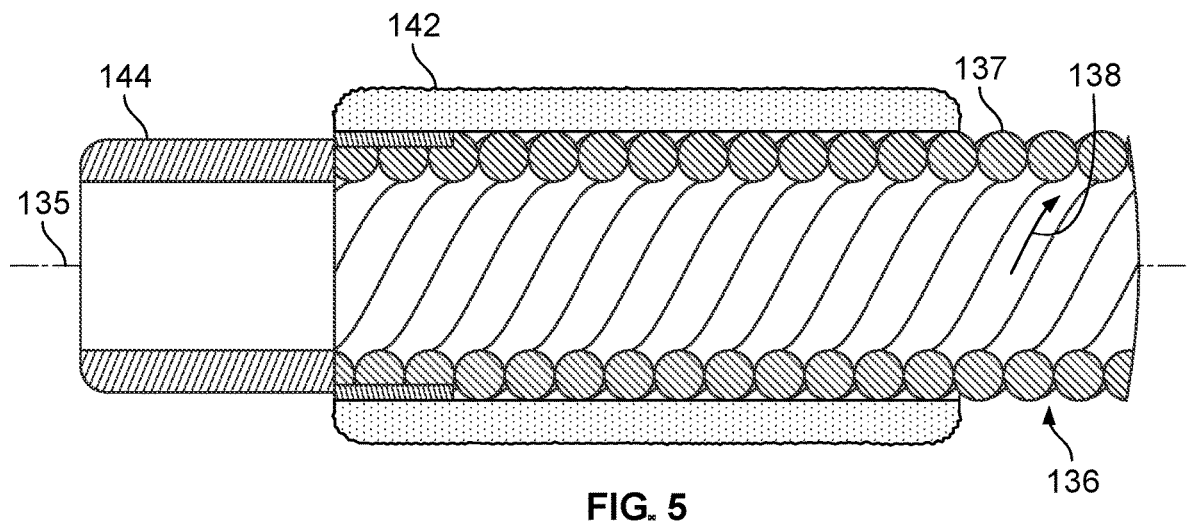
FIG. 5 is a transverse cross-sectional view of a distal tip of the rotational atherectomy device of FIG. 2.

Referring now to FIG. 5, the drive shaft 136 of the rotational atherectomy device can be equipped with the concentric tip member 144 and the distal stability element 142 in an arrangement that covers the distal-most end of the torque-transmitting coil 137. As such, the stenotic lesion 107 (FIG. 4) is initially engaged with the concentric tip member 144 and the distal stability element 142 before engaging an exterior of the torque-transmitting coil 137. In this embodiment, the distal tip member is welded (e.g., a butt weld) or otherwise fixed to a distal-most end of the torque-transmitting coil 137 of the drive shaft 136 so that the entirety of the distal tip member 144 is positioned axially distal of the torque-transmitting coil 137. Also, the distal stability element 142 is a cylindrical structure in the embodiment, which is welded or otherwise fixed to the distal-most end of the torque-transmitting coil 137 so that the distal stability element 142 is positioned radially outward of the coil diameter. As such, the distal-most end of the torque-transmitting coil of the drive shaft 136 is concealed by the distal stability element 142 and the concentric tip member 144. In this embodiment, both the distal stability element 142 and the concentric tip member 144 comprise metallic cylindrical members that are axially aligned with a central axis of the drive shaft 136, but they are different in size and in abrasiveness. The distal stability element 142 has an inner diameter that surrounds an exterior coil diameter of the drive shaft 136 (and thus the maximum outer diameter of the distal stability element 142 is larger than the coil diameter), and the concentric tip member 144 has an outer diameter that is substantially the same as the coil diameter. Also, the distal stability element 142 has an abrasive outer coating. For example, in some embodiments, a diamond coating (or other suitable type of abrasive coating) is disposed on the outer surface of the distal stability element 142. The concentric tip member 144 in this embodiment has smooth exterior surface that is less abrasive than that of the distal stability element 142. In some cases, the smooth initial surface of the concentric tip member 144 followed by the abrasive surface on the distal stability element 142 can help facilitate the initial expansion and abrasion pilot path through the stenotic lesion 107 in the targeted vessel 105. Both the distal stability element 142 and the concentric tip member 144 may comprise a biocompatible material, such as a higher-density biocompatible material. For example, in some embodiments, each of the distal stability element 140 and the concentric tip member 144 may comprise a metallic material such as stainless steel, tungsten, molybdenum, iridium, cobalt, cadmium, and the like, and alloys thereof. Also, in this embodiment, the distal stability element 140 and the concentric tip member 144 have a fixed outer diameter. That is, the distal stability element 140 and the concentric tip member 144 are not an expandable member in the depicted embodiment.

Figure 7:
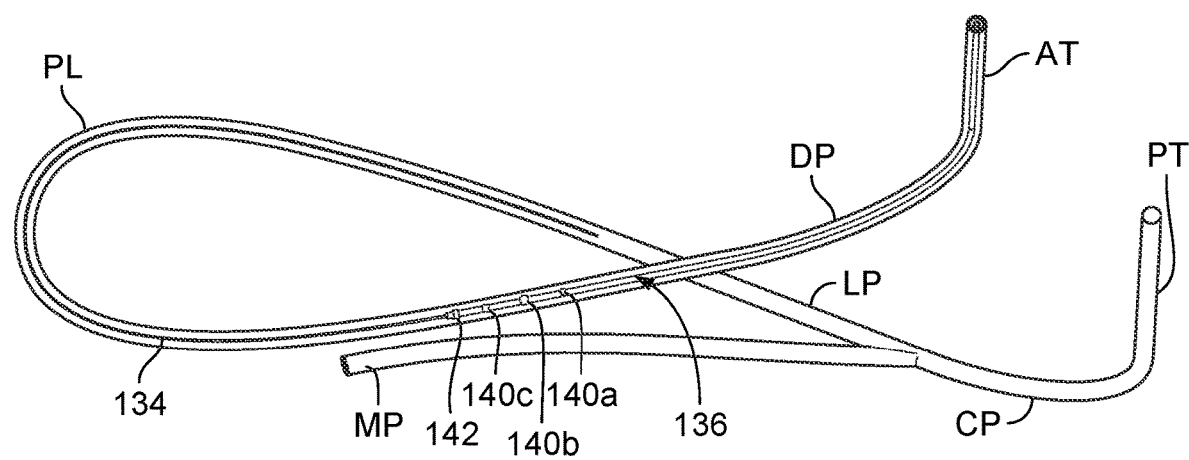
FIG. 7 is a magnified perspective view of the distal portion of the example rotational atherectomy system of FIG. 6 in the pedal blood vessel below the ankle.

Referring now to FIGS. 6-7, some embodiments of the rotational atherectomy system 100 can remove (partially or completely) one or more stenotic lesions in a targeted pedal artery below the ankle. For example, in the depicted implementation, the drive shaft 136 of the rotational atherectomy system 100 is navigated through the anterior tibial (AT) artery into the dorsalis pedis (DP) artery toward the pedal loop (LP). As previously described, the components along the distal end portion of the drive shaft 136 can have an orientation, relative spacing, and relative size so as to achieve an efficient access path to such small arteries, including those where the vessel interior diameter is often 3 mm or less and the access path follows a tortuous route. In use, the system 100 includes the guidewire 134, which is advanced into the target pedal artery below the ankle. In the example shown in FIGS. 6-7, the guidewire 134 is navigated through the anterior tibial (AT) artery into the dorsalis pedis (DP) artery, and into the pedal loop (LP). Such a guidewire position can be useful for rotational atherectomy that targets one or more lesions in the dorsalis pedis artery (DP). It should be understood from the description here that the targeted pedal artery may additionally or alternatively include the pedal loop (LP), the anterior tibial (AT) artery below the ankle, the posterior tibial artery (PT) below the ankle, the common plantar (CP) artery, the medial plantar (MP) artery. After advancement of the guidewire 134, the drive shaft 136 and sheath 132 (FIG. 1) are advanced over the proximal end of the guidewire 134 such that the proximal end of the guidewire 134 passes through the entirety of the drive shaft 136 and the handle assembly 110 (FIG. 1) to protrude rearwardly from the proximal end of the handle assembly 110. Optionally, the drive shaft 136 and sheath 132 are advanced through a relatively small introducer sheath in a patient's leg, such as a 4-French introducer sheath (FIG. 1).

Still referring to FIGS. 6-7, as the distal end portion of the drive shaft 136 is navigated toward the targeted pedal artery (preferably, under medical imaging), the concentric tip member 144 (followed by the abrasive surface on the distal stability element 142) can be used to initially form a pilot path through the stenotic lesion in the pedal artery. From there, the user can select a rotational speed setting (e.g., using user interface buttons 117a-b on the handle assembly) so that the abrasive elements 140a-c can abrade the stenotic material and achieve an orbital path during rotation (e.g., an orbital path that is greater in size than a maximum stationary diameter of the abrasive elements 140a-c. The handle assembly 110 (FIG. 1) can be used, via the actuator 116 to translate the abrasive elements 140a-c in reciprocating movement (distally and proximally) for multiple passes through the stenotic lesion in the pedal artery during high speed rotation of the abrasive elements 140a-c in the orbital path.

Accordingly, the drive shaft 136 of the rotational atherectomy system 100 can have a configuration that provides safe and repeatable navigation into smaller blood vessels below the ankle or in the heart and effective orbital paths for abrading stenotic material in such smaller vessels. Such configurations can be particularly useful, for example as shown in FIGS. 2-7, when the rotational atherectomy system 100 implemented as a pedal loop navigable system. Additionally, the implementation of the drive shaft depicted in FIGS. 2-7 can be effective for the removal or reduction of stenotic lesions in larger vessels too (e.g., those in the leg above the ankle), thereby providing the user with options for efficiently treating a variety of arterial sites during a single procedure using a single driveshaft 136.

Referring now to FIGS. 8-9, some embodiments of the distal end portion of the drive shaft 136 include an alternative configuration of the abrasive burrs that also provides a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the components along the distal end portion of the drive shaft 136 are similar to those described in connection with FIGS. 2-3, except that the distal and proximal abrasive elements 140d have a smaller size than the intermediate abrasive element 140b. For example, the torque-transmitting coil 137, the filar wind direction 138, the rotation direction 139, the intermediate abrasive element 140b, the optional distal stability element 142, and the optional distal tip member 144 have a similar configuration as previously described in connection with FIGS. 2-3. Here, as shown in FIGS. 8-9, the set of abrasive burrs along the end length of the torque-transmitting coil 137 include distal and proximal abrasive burrs 140d, which have a size that is smaller than the intermediate abrasive burr 140b. As shown in FIG. 8, the distal and proximal abrasive burrs 140d have a diameter G1 and the intermediate abrasive burr 140b has a larger diameter G2 (both G1 and G2 are larger than the coil diameter A described in connection with FIG. 2). For example, the distal and proximal abrasive burrs 140d can have a diameter G1 of 1.0 mm to 1.15 mm, and particularly 1.1 mm in the depicted embodiment here (e.g., nominal diameter of 1.1 mm before application of thin abrasive coating), and the intermediate abrasive burr 140b can have a diameter G2 of 1.2 mm to 1.33 mm, and particularly 1.25 mm in the depicted embodiment here (e.g., nominal diameter of 1.25 mm before application of thin abrasive coating). As previously described, in such examples, the coil diameter A can be 0.7 mm to 0.9 mm, and preferably 0.8 mm in this depicted embodiment. Accordingly, in the depicted example, the burr-to-coil diameter ratio can be 1.3-1.4 for each smaller abrasive burr 140d mounted to the torque-transmitting coil 137, and the burr-to-coil diameter ratio can be 1.5-1.7 for the larger abrasive burr 140b mounted to the torque-transmitting coil 137. Also shown in FIG. 9, the centers of mass of the distal abrasive burr 140d, the intermediate abrasive burr 140b, and the proximal abrasive burr 140d are offset in different planes at radial spacing angle H. As previously described in connection with FIGS. 2-3, the radial spacing angle H of 5 degrees to 87.5 degrees, preferably 20 degrees to 60 degrees, and 37.5 degrees in the depicted embodiment here. As such, the combined radial angles of the all abrasive burrs 140d, 140b, and 140d is less than 175 degrees (e.g., less than 120 degrees, and preferably less than 90 degrees in the depicted embodiment) along the end length of the drive shaft.

Accordingly, similar to the embodiments described above in connection with FIGS. 2-4, the embodiment depicted in FIGS. 8-9 is provided in the form of a "4-French introducible" device, as described above. Additionally, the abrasive burrs 140d, 140b, and 140d shown in FIGS. 8-9, the optional distal stability element 142, and the optional distal tip member 144 can collectively provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery.

Referring now to FIGS. 10-11, additional embodiments of the distal end portion of the drive shaft 136 include an alternative configuration of the abrasive burrs that also provides a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the components along the distal end portion of the drive shaft 136 are similar to those described in connection with FIGS. 8-9, except that the distal and proximal abrasive elements 140*e* have a different cutout for mounting to the torque-transmitting coil 137 so that the geometric center of the spherical element is axially aligned with the axis 135 of the torque-transmitting coil 137. For example, the torque-transmitting coil 137, the filar wind direction 138, the rotation direction 139, the intermediate abrasive element 140*b*, the optional distal stability element 142, and the optional distal tip member 144 have a similar configuration as previously described in connection with FIGS. 2-3 and 8-9. Here, as shown in FIGS. 10-11, the distal and proximal abrasive burrs 140*e* have deeper mounting slot formed therein (e.g., deeper compared to the example abrasive elements 140*d* in FIGS. 8-9) such that, when the distal and proximal abrasive burrs 140*e* are affixed to the exterior of the torque-transmitting coil 137, the geometric center of each spherical element 140*e* is axially aligned with the axis 135 of the torque-transmitting coil 137. In other words, even though the distal and proximal abrasive burrs 140*d* (FIGS. 8-9) and the distal and proximal abrasive burrs 140*e* (FIGS. 10-11) have the same diameter size, the outer spherical surface of the distal and proximal abrasive burrs 140*e* (FIGS. 10-11) is closer to the central axis 135 of the torque-transmitting coil 137. Due to the mounting slot formed in each of the distal and proximal abrasive burrs 140*e*, the center of mass of the burr 140*e* is offset from the central axis while the geometric center of the burr 140*e* is axially aligned with the axis. Also, as shown in FIG. 11, the centers of mass of the distal abrasive burr 140*e*, the intermediate abrasive burr 140*b*, and the proximal abrasive burr 140*e* are offset in different planes at radial spacing angle H. As previously described in connection with FIGS. 2-3 and 8-9, the radial spacing angle H of 5 degrees to 87.5 degrees, preferably 20 degrees to 60 degrees, and 37.5 degrees in the depicted embodiment here. As such, the combined radial angles of the all abrasive burrs 140*e*, 140*b*, and 140*e* is less than 175 degrees (e.g., less than 120 degrees, and preferably less than 90 degrees in the depicted embodiment) along the end length of the drive shaft.

Here again, similar to the embodiments described above in connection with FIGS. 2-4 and 8-9, the embodiment depicted in FIGS. 10-11 is provided in the form of a "4-French introducible" device, as described above. Additionally, the abrasive burrs 140*e*, 140*b*, and 140*e* shown in FIGS. 10-11, the optional distal stability element 142, and the optional distal tip member 144 can collectively provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery.

Referring now to FIGS. 12-13, additional embodiments of the distal end portion of the drive shaft 136 include an alternative configuration of the abrasive burrs that also provides a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the components along the distal end portion of the drive shaft 136 are similar to those described in connection with FIGS. 8-9, except that one of the distal and proximal abrasive elements (the distal abrasive element 140*f* in this example) has a center of mass that is offset in the same plane as the intermediate abrasive element 140*b*. For example, the torque-transmitting coil 137, the filar wind direction 138, the rotation direction 139, the intermediate abrasive element 140*b*, the optional distal stability element 142, and the optional distal tip member 144 have a similar configuration as previously described in connection with FIGS. 2-3 and 8-9. And, similar to the embodiment shown in FIGS. 8-9, the distal abrasive burr 140*e* and proximal abrasive burr 140*d* have the same diameter size (e.g., diameter size G1 described above in FIG. 8), which is smaller than the intermediate abrasive burr 140*b* (e.g., diameter size G2 described above in FIG. 8). However, as shown in FIGS. 12-13, the abrasive burrs are offset only in two longitudinal planes. For example, only one of the abrasive burrs (element 140*d* in this example) has a center of mass that is offset in a different plane at radial spacing angle H, while the remaining abrasive burrs 140*f* and 140*b* have centers of mass that are offset in the same longitudinal plane. As previously described in connection with FIGS. 2-3 and 8-9, the radial spacing angle H of 5 degrees to 87.5 degrees, preferably 20 degrees to 60 degrees, and 37.5 degrees in the depicted embodiment here. As such, the combined radial angles of the all abrasive burrs 140*e*, 140*b*, and 140*e* is less than 175 degrees (e.g., less than 120 degrees, and preferably less than 90 degrees in the depicted embodiment) along the end length of the drive shaft.

Accordingly, similar to the embodiments described above in connection with FIGS. 2-4 and 8-11, the embodiment depicted in FIGS. 12-13 is provided in the form of a "4-French introducible" device, as described above. Additionally, the abrasive burrs 140*f*, 140*b*, and 140*d* shown in FIGS. 12-13, the optional distal stability element 142, and the optional distal tip member 144 can collectively provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery.

Referring now to FIGS. 14-15, further embodiments of the distal end portion of the drive shaft 136 include an alternative configuration of the abrasive burrs that also provides a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the components along the distal end portion of the drive shaft 136 are similar to those described in connection with FIGS. 8-9, except that all of the distal and proximal abrasive elements 140*f* and the intermediate abrasive element have centers of mass offset in the same plane. For example, the torque-transmitting coil 137, the filar wind direction 138, the rotation direction 139, the intermediate abrasive element 140*b*, the optional distal stability element 142, and the optional distal tip member 144 have a similar configuration as previously described in connection with FIGS. 2-3 and 8-9. And, similar to the embodiment shown in FIGS. 8-9, the distal abrasive burr 140f and proximal abrasive burr 140f have the same diameter size (e.g., diameter size G1 described above in FIG. 8), which is smaller than the intermediate abrasive burr 140b (e.g., diameter size G2 described above in FIG. 8). However, as shown in FIGS. 14-15, the abrasive burrs are offset only in a single longitudinal plane.

Here again, similar to the embodiments described above in connection with FIGS. 2-4 and 8-13, the embodiment depicted in FIGS. 14-15 is provided in the form of a "4-French introducible" device, as described above. Additionally, the abrasive burrs 140f, 140b, and 140f shown in FIGS. 14-15, the optional distal stability element 142, and the optional distal tip member 144 can collectively provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery.

Figure 16:
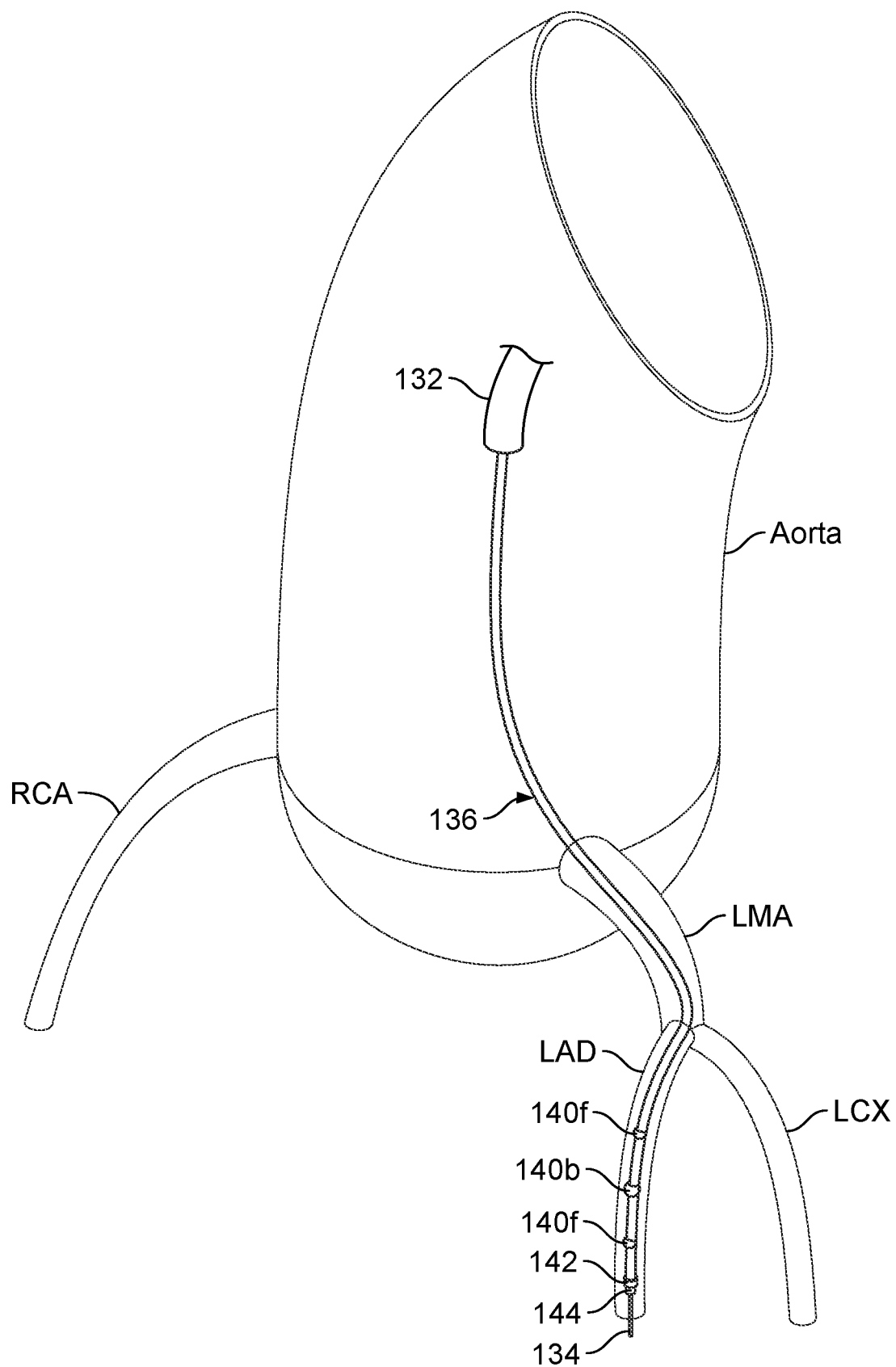
FIG. 16 is a perspective view of the distal portion of the example rotational atherectomy device of FIG. 14 in a coronary blood vessel, in accordance with some embodiments.

Referring now to FIG. 16, some embodiments of the rotational atherectomy system 100 can advance through the tortuous path into a branch coronary artery (e.g., the left anterior descending coronary artery or the left circumflex coronary artery) of a heart to remove (partially or completely) one or more stenotic lesions in a targeted branch coronary artery. For example, in the depicted implementation, the drive shaft 136 of the rotational atherectomy system 100 is navigated through the aorta into the left main artery (LMA) toward the left anterior descending artery (LAD) of the heart. In the depicted embodiment, the distal end portion of the drive shaft 136 includes the configuration depicted in FIGS. 14-15, but it should be understood from the description herein that other embodiments (e.g., FIGS. 2-3, 8-13, and 17-24) can also be implemented in the targeted branch coronary artery.

As previously described, the components along the distal end portion of the drive shaft 136 can have an orientation, relative spacing, and relative size so as to achieve an efficient access path to such small arteries, including those where the vessel interior diameter is often 3 mm or less and the access path follows a tortuous route. In use, the system 100 includes the guidewire 134, which is advanced into the target branch coronary artery of the heart. In the example shown in FIG. 16, the guidewire 134 is navigated through the aorta into the left main artery (LMA) toward the left anterior descending artery (LAD) of the heart. Such a guidewire position can be useful for rotational atherectomy that targets one or more lesions in the left anterior descending artery (LAD). It should be understood from the description here that the targeted branch coronary artery may alternatively include the left circumflex artery (LCX) or other branch artery along the heart. After advancement of the guidewire 134, the drive shaft 136 and sheath 132 (FIG. 1) are advanced over the proximal end of the guidewire 134 such that the proximal end of the guidewire 134 passes through the entirety of the drive shaft 136 and the handle assembly 110 (FIG. 1) to protrude rearwardly from the proximal end of the handle assembly 110. Optionally, the drive shaft 136 and sheath 132 are advanced through a relatively small introducer sheath in a patient's leg, such as a 4-French introducer sheath (FIG. 1).

Still referring to FIG. 16, as the distal end portion of the drive shaft 136 is navigated toward the targeted branch coronary artery (preferably, under medical imaging), the concentric tip member 144 (followed by the abrasive surface on the distal stability element 142) can be used to initially form a pilot path through the stenotic lesion in the branch coronary artery. From there, the user can select a rotational speed setting (e.g., using user interface buttons 117a-b on the handle assembly) so that the abrasive elements 140f, 140b, and 140f can abrade the stenotic material and achieve an orbital path during rotation (e.g., an orbital path that is greater in size than a maximum stationary diameter of the larger abrasive element 140b. The handle assembly 110 (FIG. 1) can be used, via the actuator 116 to translate the abrasive elements 140f, 140b, and 140f in reciprocating movement (distally and proximally) for multiple passes through the stenotic lesion in the pedal artery during high speed rotation of the abrasive elements 140f, 140b, and 140f in the orbital path.

Accordingly, the drive shaft 136 of the rotational atherectomy system 100 can have a configuration that provides safe and repeatable navigation into smaller blood vessels below the ankle or in the heart and effective orbital paths for abrading stenotic material in such smaller vessels. Such configurations can be particularly useful, for example as shown in FIGS. 2-7, when the rotational atherectomy system 100 implemented as a pedal loop navigable system. Additionally, the implementation of the drive shaft depicted in FIGS. 2-7 can be effective for the removal or reduction of stenotic lesions in larger vessels too (e.g., those in the leg above the ankle), thereby providing the user with options for efficiently treating a variety of arterial sites during a single procedure using a single driveshaft 136.

Referring now to FIGS. 17-18, additional embodiments of the distal end portion of the drive shaft 136 include an alternative configuration of the abrasive burrs that also provides a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the components along the distal end portion of the drive shaft 136 are similar to those described in connection with FIGS. 8-9, except that the distal and proximal abrasive elements 140g have a cylindrical shape and are mounted in axial alignment with the axis 135 of the torque-transmitting coil 137. For example, the torque-transmitting coil 137, the filar wind direction 138, the rotation direction 139, the intermediate abrasive element 140b, the optional distal stability element 142, and the optional distal tip member 144 have a similar configuration as previously described in connection with FIGS. 2-3 and 8-9. Here, as shown in FIGS. 17-18, the distal and proximal abrasive burrs 140g have a tubular shape that is similar to that of the distal stability element 142 (refer also to FIG. 5 for details of the tubular structure) such that, when the distal and proximal abrasive burrs 140g are affixed to the exterior of the torque-transmitting coil 137, the center of mass and the geometric center of each cylindrical element 140g are axially aligned with the central axis 135 of the torque-transmitting coil 137. Also, the distal and proximal abrasive burrs 140g (FIGS. 17-18) have the same diameter size (e.g., diameter size G1 described above in FIG. 8), which is smaller than the intermediate abrasive burr 140b (e.g., diameter size G2 described above in FIG. 8). However, as shown in FIGS. 17-18, only one of the abrasive burrs (element 140b in this example) has a center of mass offset from the central axis 135. Similar to the embodiments described above in connection with FIGS. 2-4 and 8-15, the embodiment depicted in FIGS. 17-18 is provided in the form of a "4-French introducible" device, as described above. Additionally, the abrasive burrs 140g, 140b, and 140g shown in FIGS. 17-18, the optional distal stability element 142, and the optional distal tip member 144 can collectively provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery.

Referring now to FIGS. 19-20, additional embodiments of the distal end portion of the drive shaft 136 include an alternative configuration of the abrasive burrs that also provides a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the components along the distal end portion of the drive shaft 136 are similar to those described in connection with FIGS. 17-18, except that the distal and proximal abrasive elements 140h have a cylindrical shape with a shorter axial length than the cylindrical elements 140g depicted in FIGS. 17-18. For example, the torque-transmitting coil 137, the filar wind direction 138, the rotation direction 139, the intermediate abrasive element 140b, the optional distal stability element 142, and the optional distal tip member 144 have a similar configuration as previously described in connection with FIGS. 2-3 and 8-9. Here, as shown in FIGS. 19-20, the distal and proximal abrasive burrs 140h have a tubular shape with a diameter similar to that of the distal stability element 142 (refer also to FIG. 5 for details of the tubular structure) but with an axial length that shorter than that of the distal stability element 142 (e.g., less than half of the axial length of the distal stability element 142 in this embodiment). For example, the axial length of each of the distal and proximal abrasive burrs 140h is 0.6 mm to 0.8 mm, and particularly 0.76 mm in the embodiment (which is also less than the coil diameter in this embodiment). In this example, the axial length of distal abrasive element 142 is 1.75 mm to 2 mm, and particularly 1.9 mm in the embodiment (which is greater than the coil diameter in this embodiment). As previously described, the distal and proximal abrasive burrs 140h are affixed to the exterior of the torque-transmitting coil 137 so that the center of mass and the geometric center of each cylindrical element 140h are axially aligned with the central axis 135 of the torque-transmitting coil 137. Also, the distal and proximal abrasive burrs 140h (FIGS. 19-20) have the same diameter size (e.g., diameter size G1 described above in FIG. 8), which is smaller than the intermediate abrasive burr 140b (e.g., diameter size G2 described above in FIG. 8). As shown in FIGS. 19-20, only one of the abrasive burrs (element 140b in this example) has a center of mass offset from the central axis 135. Similar to the embodiments described above in connection with FIGS. 2-4, 8-15 and 17-18, the embodiment depicted in FIGS. 17-18 is provided in the form of a "4-French introducible" device, as described above. Additionally, the abrasive burrs 140g, 140b, and 140g shown in FIGS. 19-20, the optional distal stability element 142, and the optional distal tip member 144 can collectively provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery.

Referring now to FIGS. 21-22, additional embodiments of the distal end portion of the drive shaft 136 include an alternative configuration of the abrasive burrs that also provides a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the components along the distal end portion of the drive shaft 136 are similar to those described in connection with FIGS. 2-3, except that (i) those components are mounted within a more compact end length E' (shorter that end length E shown in FIG. 2), (ii) the distal and proximal abrasive elements 140i have a smaller size than the intermediate abrasive element 140b, and (iii) the distal stability element 142' has a smaller size (smaller than the distal stability element 142 shown in FIG. 2). For example, the torque-transmitting coil 137, the filar wind direction 138, the rotation direction 139, the intermediate abrasive element 140b, and the optional distal tip member 144 have a similar configuration as previously described in connection with FIGS. 2-3. Here, as shown in FIGS. 21-22, the abrasive burrs 140i, 140b, and 140i can be mounted to the coil 137 so as to provide a more compact end length E' between the proximal-most abrasive element 140i and the distal-most tip of the drive shaft 136, which can be effective in treating stenotic lesions 107 in small arteries, such as those in the feet below the ankle or those in the coronary arteries. For example, the more compact end length E can be less than 1.8 cm from the distal-most tip of the drive shaft 136, preferably 1.3 cm to 1.6 cm, and about 1.5 cm (0.60 inches) in the depicted embodiment. Such an end length E can be relative compact compared to the overall length of torque-transmitting coil 137 (e.g., refer to length B in FIG. 2, which can be 150 cm to 250 cm, and about 197 cm (77.5 inches) in this embodiment). As such, the end length E' can be less than 0.8% of the overall length B. In some embodiments, the ratio of the overall length B to the end length E is about 120:1 to 140:1, and about 129:1 in the depicted embodiment. Also, in the depicted embodiment, the abrasive burrs 140i, 140b, and 140i in the more compact end length E' includes a total of three discrete elements that are spaced apart from each other. In other embodiments, one, two, three, four, or five discrete abrasive elements are included in the set of abrasive elements within the more compact end length E'. Additionally, within the more compact end length E' of the drive shaft 136, the distal-most abrasive burr 140i can be spaced from the distal-most end of the shaft by an extension length C', with the intermediate abrasive burr 140b being spaced therefrom by a burr spacing distance D', and the proximal-most abrasive burr 140i being spaced apart therefrom by the same burr spacing distance D'. In the depicted embodiment, the extension length C' is the same as the burr spacing distance D'. For example, the extension length C' can be 4 mm to 6 mm, and about 5 mm (0.20 inches) in the depicted embodiment, while the burr spacing distance D' can likewise be 4 mm to 6 mm, and about 5 mm (0.20 inches) in the depicted embodiment.

Still referring to FIGS. 21-22, the set of abrasive burrs along the end length E' of the torque-transmitting coil 137 include the distal and proximal abrasive burrs 140*i*, which have a size that is smaller than the intermediate abrasive burr 140*b*. As shown in FIG. 21, the distal and proximal abrasive burrs 140*d* have a diameter G3 and the intermediate abrasive burr 140*b* has a larger diameter G2 (both G3 and G2 are larger than the coil diameter A described in connection with FIG. 2). For example, the distal and proximal abrasive burrs 140*i* can have a diameter G3 of 0.9 mm to 1.1 mm, and particularly 1.0 mm in the depicted embodiment here (e.g., nominal diameter of 1.0 mm before application of thin abrasive coating), and the intermediate abrasive burr 140*b* can have a diameter G2 of 1.2 mm to 1.33 mm, and particularly 1.25 mm in the depicted embodiment here (e.g., nominal diameter of 1.25 mm before application of thin abrasive coating). As previously described, in such examples, the coil diameter A can be 0.7 mm to 0.9 mm, and preferably 0.8 mm in this depicted embodiment. Accordingly, in the depicted example, the burr-to-coil diameter ratio can be 1.2-1.3 for each smaller abrasive burr 140*i* mounted to the torque-transmitting coil 137, and the burr-to-coil diameter ratio can be 1.5-1.7 for the larger abrasive burr 140*b* mounted to the torque-transmitting coil 137. Also shown in FIG. 22, the centers of mass of the distal abrasive burr 140*i*, the intermediate abrasive burr 140*b*, and the proximal abrasive burr 140*i* are offset in different planes at radial spacing angle H. As previously described in connection with FIGS. 2-3, the radial spacing angle H of 5 degrees to 87.5 degrees, preferably 20 degrees to 60 degrees, and 37.5 degrees in the depicted embodiment here. As such, the combined radial angles of the all abrasive burrs 140*i*, 140*b*, and 140*i* is less than 175 degrees (e.g., less than 120 degrees, and preferably less than 90 degrees in the depicted embodiment) along the end length E' of the drive shaft.

Still referring to FIGS. 21-22, the some embodiments of the drive shaft 136 can include distal stability element 142' having a shorter axial length. For example, the distal stability element 142' can have an axial length that smaller than the coil diameter of the torque-transmitting coil 137 (refer to coil diameter A described in connection with FIG. 2). In this embodiment, the axial length of the distal stability element 142' is 0.6 mm to 0.8 mm, and particularly 0.76 mm in the embodiment. Here, the distal stability element 142' has a cylindrical shape and can have an outer diameter that is greater than the distal and proximal abrasive burrs 140*i* (e.g., diameter size G3 described above), which is smaller than the intermediate abrasive burr 140*b* (e.g., diameter size G2 described above). Similar to the embodiments described above in connection with FIGS. 2-4, 8-15 and 17-20, the embodiment depicted in FIGS. 21-22 is provided in the form of a "4-French introducible" device, as described above. Additionally, the abrasive burrs 140*i*, 140*b*, and 140*i* shown in FIGS. 21-22, the optional distal stability element 142', and the optional distal tip member 144 can collectively provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery.

Referring now to FIGS. 23-24, additional embodiments of the distal end portion of the drive shaft 136 include an alternative configuration of the abrasive burrs that also provides a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the components along the distal end portion of the drive shaft 136 are similar to those described in connection with FIGS. 21-22, except that all of the distal abrasive element 140*c*, the intermediate abrasive element 140*b*, and the proximal abrasive element 140*a* have the same diameter size (refer to diameter G described above in connection with FIG. 2). For example, the torque-transmitting coil 137, the filar wind direction 138, the rotation direction 139, the intermediate abrasive element 140*b*, the optional distal stability element 142', and the optional distal tip member 144 have a similar configuration as previously described in connection with FIGS. 21-22. And, similar to the embodiment shown in FIGS. 2-3, the distal abrasive burr 140*c* and the proximal abrasive burr 140*a* have the same diameter size as the intermediate abrasive burr 140*b*. However, as shown in FIGS. 23-24, the abrasive burrs 140*a*-*c* are mounted in the more compact end length E' (described above in FIGS. 21-22). Also shown in FIG. 24, the centers of mass of the distal abrasive burr 140*c*, the intermediate abrasive burr 140*b*, and the proximal abrasive burr 140*a* are offset in different planes at radial spacing angle H. As previously described in connection with FIGS. 2-3, the radial spacing angle H of 5 degrees to 87.5 degrees, preferably 20 degrees to 60 degrees, and 37.5 degrees in the depicted embodiment here. As such, the combined radial angles of the all abrasive burrs 140*a*-*c* is less than 175 degrees (e.g., less than 120 degrees, and preferably less than 90 degrees in the depicted embodiment) along the more compact end length E' of the drive shaft 136.

Accordingly, similar to the embodiments described above in connection with FIGS. 2-4, 8-15 and 17-22, the embodiment depicted in FIGS. 23-24 is provided in the form of a "4-French introducible" device, as described above. Additionally, the abrasive burrs 140*a*-*c* shown in FIGS. 23-24, the optional distal stability element 142', and the optional distal tip member 144 can collectively provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery.

Referring now to FIGS. 25-26, additional embodiments of the distal end portion of the drive shaft 136 include an alternative configuration of the abrasive burrs that also provides a relative orientation, relative spacing, and relative sizing along the torque-transmitting coil 137 of the drive shaft 136 so as to achieve an efficient access path to such small arteries, including those where the vessel interior diameter is often 3 mm or less and the access path follows a tortuous route. In the depicted embodiment, the components along the distal end portion of the drive shaft 136 are similar to those described in connection with FIGS. 19-20, except that the distal and proximal abrasive elements 140*j* coaxially mounted to the torque transmitting coil 137 have a spherical shape (rather than the cylindrical shape of element 140*h* in FIG. 19) and the optional distal stability element 142 is removed (such that the abrasive elements 140*j* and 140*b* are positioned closer to the distal-most end as compared to FIG. 19). For example, the torque-transmitting coil 137, the filar wind direction 138, the rotation direction 139, the intermediate abrasive element 140*b*, and the optional distal tip member 144 have a similar configuration as previously described in connection with FIGS. 2-3 and 8-9. Here, as shown in FIGS. 25-26, the distal and proximal abrasive burrs 140*j* have a spherical shape that is mounted coaxially to the torque transmitting coil 137, and the intermediate abrasive burr 140*b* has a center of mass that is offset from the central axis 135. Much like the concentric abrasive burrs 140*h* depicted in FIG. 19, the distal and proximal abrasive burrs 140*j* in this embodiment are affixed to the exterior of the torque-transmitting coil 137 so that the center of mass and the geometric center of each spherical element 140*j* are axially aligned with the central axis 135 of the torque-transmitting coil 137. Also, the distal and proximal abrasive burrs 140*j* (FIGS. 25-26) have the same diameter size (e.g., diameter size G1 described above in FIG. 8), which is smaller than the intermediate abrasive burr 140*b* (e.g., diameter size G2 described above in FIG. 8). In some embodiments, the distal and proximal abrasive burrs 140*j* have the same diameter size of 1.0 mm to 1.15 mm, and particularly 1.1 mm in the depicted embodiment here (e.g., nominal diameter of 1.1 mm before application of thin abrasive coating), and the intermediate abrasive burr 140*b* can have a diameter of 1.2 mm to 1.33 mm, and particularly 1.25 mm in the depicted embodiment here (e.g., nominal diameter of 1.25 mm before application of thin abrasive coating). As shown in the example in FIGS. 25-26, only one of the abrasive burrs 140*j*, 140*b*, and 140*j* mounted to the shaft 137 (element 140*b* in this example) has a center of mass offset from the central axis 135. Additionally, the distal-most abrasive burr 140*j* can be spaced from the distal-most face of the shaft 136 by a tip length C", with the intermediate abrasive burr 140*b* being spaced therefrom by a burr spacing distance D", and the proximal-most abrasive burr 140*j* being spaced apart therefrom by the same burr spacing distance D". In the depicted embodiment, the tip length C" is a different length than the burr spacing distance D". For example, the tip length C" can be 0.6 mm to 1.1 mm, and about 1 mm (preferably about 0.04 inches) in the depicted embodiment, while the burr spacing distance D" can be 4 mm to 6 mm, and about 5 mm (preferably about 0.20 inches) in the depicted embodiment. Accordingly, in such embodiments, all of the abrasive burrs 140*j*, 140*b*, and 140*j* in the series are positioned significantly close to the distal-most tip of the drive shaft 136. For example, in this embodiment, the proximal-most abrasive burr 140*j* can be coaxially mounted to the torque-transmitting coil at a position that is less than one inch from the distal-most tip of the drive shaft 136, and preferably no greater than 0.5 inches from the distal-most end of the torque-transmitting coil.

Similar to the embodiments described above in connection with FIGS. 2-4, 8-15 and 17-18, the embodiment depicted in FIGS. 25-26 is provided in the form of a "4-French introducible" device, as described above. Additionally, the abrasive burrs 140*j*, 140*b*, and 140*j* shown in FIGS. 25-26, and the optional distal tip member 144 can collectively provide a relative orientation, relative spacing, and relative sizing along the torque-transmitting coil 137 so as to advantageously advance through a relatively small percutaneous access point, such as an access point in a patient's upper leg having a small introducer sheath (e.g., refer to FIG. 1 above) for subsequent advancement into the patient's foot or heart to remove (fully or partially) stenotic material from a targeted artery.

Figure 27:
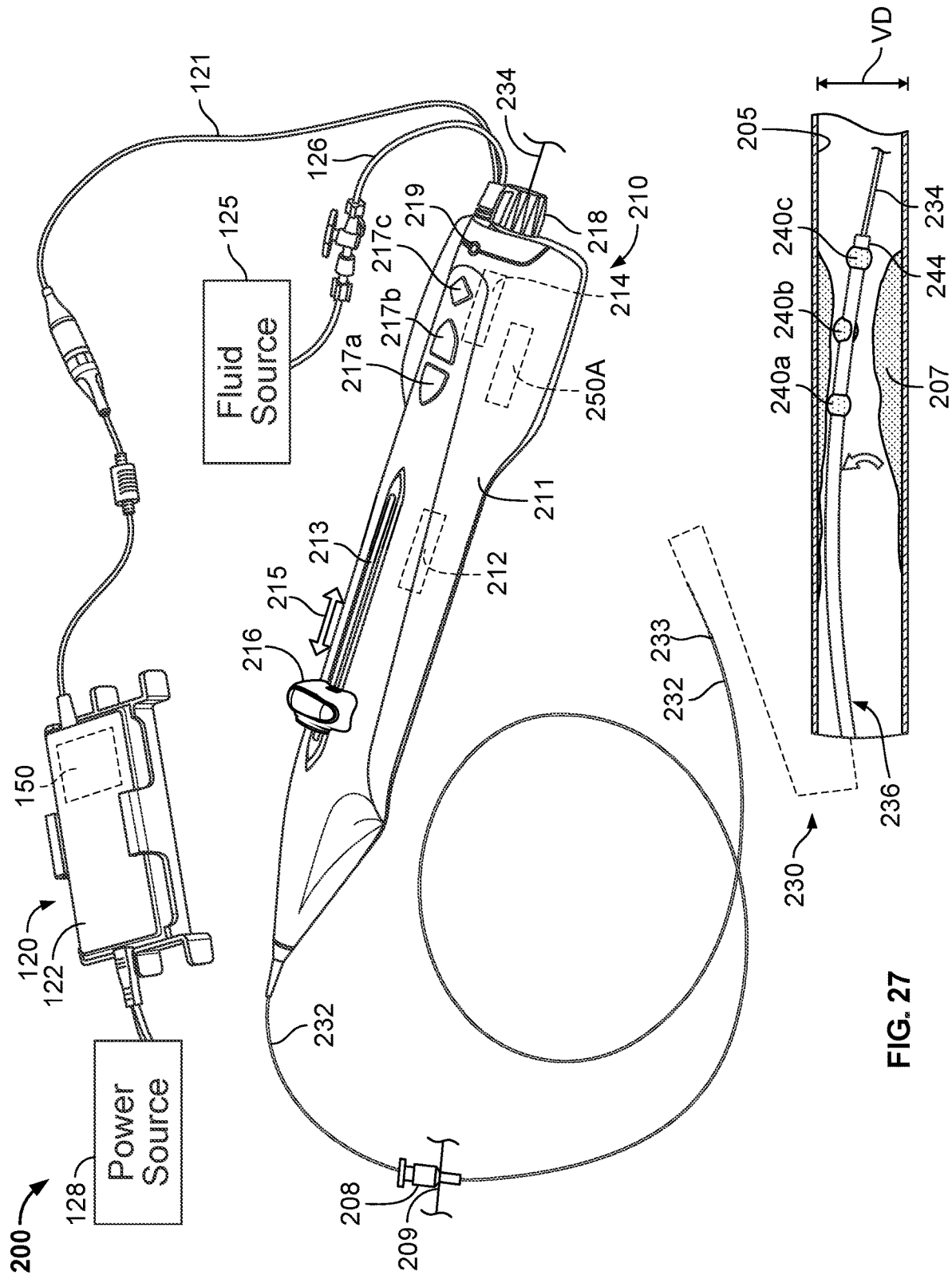
FIG. 27 is a perspective view of an example rotational atherectomy system, in accordance with some embodiments.

Referring to FIG. 27, in some embodiments a rotational atherectomy system 200 for removing (partially or completely) a stenotic lesion 207 from a targeted blood vessel 205 can include an actuator handle assembly 210 that controls movement of an elongate flexible drive shaft assembly 230. The drive shaft assembly 230 includes a flexible drive shaft 236, and a distal end portion of the driveshaft 236 includes one or more abrasive elements 240*a-c* configured to abrade the stenotic lesion 207 in the targeted vessel 205. In some embodiments, the rotational atherectomy system 200 shares features with the rotational atherectomy system 100 (e.g., including power source 128, power adapter 120, and a fluid source 125).

The abrasive elements 240*a-c* can have a selected configuration and relative sizing along the distal end portion of the drive shaft 236 so as to improve navigation into smaller blood vessels below the ankle or in the heart while also achieving an effective orbital path for abrading the stenotic material 207 in those vessels. (In the depicted example, the targeted blood vessel 205 has a vessel diameter VD of 3 mm or less, and about 2.5 mm as shown, while the initial path through the stenotic lesion is significantly smaller than that.) Optionally, the abrasive elements 240 and drive shaft 236 can have a selected configuration and relative sizing (e.g., FIGS. 2-3, 8-15, 17-26) that advantageously provides advancement through a small percutaneous introducer 208 (e.g., sized to slidably receive instruments of 4-French diameter or smaller) at a percutaneous opening 209 in a patient's leg, and can further navigate through a stenotic lesion 207 in a small artery 205, such as those below the ankle (e.g., in the feet) or coronary arteries (e.g., in the left anterior descending coronary artery or the left circumflex coronary artery) prior to sweeping a larger orbital path (during rotation of the driveshaft 236) for abrading the stenotic material 207. For example, in the depicted implementation shown in FIG. 27, the drive shaft 236 and abrasive elements 240*a-c* have the configuration described above in connection with FIG. 26-25 (e.g., drive shaft 136 and abrasive elements 140*j*, 140*b*, and 140*j*). It should be understood from the description herein that other configurations of the abrasive elements and features along the distal end of the drive shaft (such as those options depicted in FIGS. 2-3, 8-15, and 17-24) can be implemented in the system 200 of FIG. 27.

The system 200 can also include the power adapter 120 and the fluid source 125 (e.g., a saline bag) connectable to the actuator handle assembly 210, and the actuator handle assembly 210 can house therein an electric motor 212 (configured to drive rotation of the driveshaft 236) and fluid pump 214 (configured to urge a fluid such as saline toward the distal end portion of the driveshaft 236. As described in more detail below, the controller 150 for activating the electric motor 212 and the pump 214 (responsive to inputs at the user interface buttons 216 and 217*a-c* of the handle assembly 210 in addition to the position of the user interface button 216 along the actuator slot 213) can be contained inside a housing 122 of the power adapter 120 so that it is reusable with subsequent handle assemblies after the first handle assembly 210 is discarded (a single-use handle assembly). Alternatively, a controller 250A for operating the electric motor 212 and the pump 214 can be contained within the housing in the handle assembly 210 (in proximity to the electric motor 212 and the pump 214), and the entire handle assembly 210 can be discarded after a single use with a patient. In both options, the handle assembly 210 can be operated by a clinician using a simplified, screenless interface to perform and control the rotational atherectomy procedure (e.g., without a graphic display screen along the handle assembly or on a separate unit connected to the handle assembly).

Still referring to FIG. 27, the elongate flexible drive shaft assembly 230 includes a sheath 232 that extends over the flexible drive shaft 236 such that the abrasive elements 240a-c on the distal end portion of the drive shaft 236 are housed within a distal-most end of the sheath 232 in a proximal position (e.g., retracted position shown in FIGS. 28 and 29). In this position, the actuator 216 is positioned at the rearmost proximal end of the slot 213. Responsive to the clinician moving (translating) the actuator 216 distally along the slot 213 for a first translation distance 203 (distally from the rearmost proximal end of the slot 213), the abrasive elements 240a-c are extended distally from the distal most end of the sheath 232 (e.g., FIGS. 30-31). From there, the clinician can translate the actuator 216 distally along the slot 213 for a second translation distance 204 (e.g., FIGS. 32-33), can optionally reciprocate the actuator 216 between the extended positions in FIGS. 31 and 33 during rotation of the drive shaft 236). Additionally, responsive to the clinician moving (translating) the actuator 216 proximally along the slot 213 at the rearmost proximal end of the slot 213 (FIG. 28), the abrasive elements 240a-c are retracted and housed within the distal most end of the sheath 232 (e.g., FIGS. 28-29). A proximal end of the sheath 232 is fixed to a distal end of the handle assembly 210. The flexible drive shaft 236 is slidably and rotatably disposed within a lumen of the sheath 232. The flexible drive shaft 236 defines a longitudinal lumen in which a guidewire 234 is slidably disposed. The guidewire 234 can extend through the handle assembly 210, the sheath 232, and the drive shaft 236 such that a proximal end of the guidewire 234 protrudes proximally from a rear port of a guidewire brake 218 at a proximal end of the handle assembly 210 while a distal end of the guidewire 234 extends distally of a distal-most end of the drive shaft 236. In this embodiment, the flexible drive shaft 236 includes a torque-transmitting coil of one or more helically wound filars that defines the longitudinal lumen along a central longitudinal axis. The drive 236 shaft is configured to rotate about the longitudinal axis while the sheath 232 remains generally stationary. Hence, during a rotational atherectomy procedure, the sheath 232 and the guidewire 234 are generally stationary while the flexible drive shaft 236 is controllably moved (e.g., rotating about the longitudinal axis and periodically longitudinally translating proximally and/or distally). The distal end of the sheath 232 includes a marker 233 such as a radiopaque marker that can be used during an atherectomy procedure to image the position of the distal end of the sheath 232.

In the depicted embodiment, the distal end portion of the driveshaft 236 (that can be selectively retracted into the sheath 232 and extended from the sheath 232) includes one or more abrasive elements 240a-c, and a (optional) concentric tip member 244 (refer to concentric tip member 144 in FIGS. 25-26). In the depicted embodiment, the one or more abrasive elements includes a set of three eccentric abrasive elements 240a-c that are fixedly mounted to an exterior of the torque-transmitting coil of the driveshaft 236 such that the distal and proximal abrasive burrs 240h have a spherical shape that is mounted coaxially to the torque transmitting coil 237, and the intermediate abrasive burr 240b has a center of mass that is offset from the central axis 235 (e.g., as in FIGS. 25-26). As such, the center of mass of each of the distal and proximal abrasive burrs 240h are aligned with the central axis of the drive shaft 236 while the center of mass of the intermediate abrasive burr 240b is offset from the central axis of the drive shaft 236. The concentric tip member 244 (refer to concentric tip member 144 in FIG. 6) is affixed to, and extends distally from, the terminal distal-most end of the torque-transmitting coil. As described in more detail above, the concentric tip member 244 has a smoother surface than the abrasive surfaces of the abrasive elements 240a-c, and the concentric tip member 244 can be configured to provide initial penetration (and, optionally, dilation) through the stenotic lesion 207 in the targeted vessel 205.

Still referring to FIG. 27, as the drive shaft 236 is rotated about its longitudinal axis, the eccentric abrasive elements 240a-c (and the portion of the drive shaft 236 to which the one or more abrasive elements 240a-c are affixed) will be urged in an orbit path relative to the central axis of the drive shaft 236 (also as described above with respect to drive shaft 136, for example, in connection with FIG. 5). In general, faster speeds (rpm) of rotation of the drive shaft 236 will result in larger diameters of the orbit (within the limits of the vessel diameter). The orbiting one or more abrasive elements 240a-c will contact the stenotic lesion 207 to abrade the lesion to a reduced size with each traversal path through the lesion 207 (i.e., small particles of the lesion will be abraded from the lesion). As described further below, contemporaneous with the rotation of the drive shaft 236, the drive shaft 236 can be translated back and forth (distally and proximally) along the longitudinal axis of the drive shaft 236. Hence, the stenotic lesion 207 can be abraded radially and longitudinally by virtue of the simultaneous translation and orbital rotation of the abrasive elements 240a-c.

Additionally, the torque-transmitting coil of the flexible drive shaft 236 is laterally flexible (similar to flexible drive shaft 136) so that the drive shaft 236 can readily advance through a tortuous arterial path (e.g., in the pedal loop or in a coronary branch artery), and so that a portion of the drive shaft 236 at, and adjacent to, the one or more abrasive elements 240 can laterally deflect when acted on by the centrifugal forces resulting from the rotation of the one or more eccentric abrasive elements 240. In the depicted embodiment, the drive shaft 236 comprises one or more helically wound wires (or filars) that provides a uniform coil diameter that is less than the diameters of all of the abrasive elements 240a-c. As described in more detail above, this relative sizing is referred to as the burr-to-coil diameter ratio, and the burr-to-coil diameter ratio can be about 1.3-1.7 for all abrasive burrs (elements 240a-c) along the torque-transmitting coil of the drive shaft. As such, the torque-transmitting coil of the flexible drive shaft 236 can achieve both sufficient lateral flexibility during navigation through a tortuous path (e.g., in a patient's foot or heart) and sufficient longitudinal rigidity to be pushed through a stenotic lesion (while transmitting torque to rotate the abrasive elements 240a-c) in a small artery. In some embodiments, the flexible drive shaft 236 shares features with the flexible drive shaft 136.

Still referring to FIG. 27, the one or more abrasive elements 240a-c (each of which may also be referred to as an abrasive burr) can comprise a biocompatible material that is coated with an abrasive media such as diamond grit, diamond particles, silicon carbide, and the like. In the depicted embodiment, the abrasive elements 240a-c includes a total of three discrete abrasive spheres/cylinders that are spaced apart from each other to facilitate both navigation to, and orbital abrading within, a targeted small artery, including those where the vessel interior diameter is often 3 mm or less and the access path follows a tortuous route. As previously described, in the depicted implementation shown in FIG. 27, the drive shaft 236 and abrasive elements 240a-c have the configuration described above in connection with FIG. 26-25 (e.g., drive shaft 136 and abrasive elements 140*j*, 140*b*, and 140*j*). As such, the distal and proximal abrasive burrs 240*h* (as in 140*j* of FIGS. 25-26) have the same diameter size (e.g., diameter size G1 described above in FIG. 8), which is smaller than the intermediate abrasive burr 240*b* (e.g., diameter size G2 described above in FIG. 8). In some embodiments, the distal and proximal abrasive burrs 240*h* have the same diameter size of 1.0 mm to 1.15 mm, and particularly 1.1 mm in the depicted embodiment here (e.g., nominal diameter of 1.1 mm before application of thin abrasive coating), and the intermediate abrasive burr 240*b* can have a diameter of 1.2 mm to 1.33 mm, and particularly 1.25 mm in the depicted embodiment here (e.g., nominal diameter of 1.25 mm before application of thin abrasive coating). The abrasive burrs 240*a-c* may be mounted to the exterior of the torque-transmitting coil of the drive shaft 236 using a biocompatible adhesive, high temperature solder, welding, press fitting, and the like. Alternatively, the one or more abrasive elements 240*a-c* can be integrally formed as a unitary structure with the filars of the drive shaft 236 (e.g., using filars that are wound in a different pattern to create an axially offset structure, or the like).

Still referring to FIG. 27, the rotational atherectomy system 200 also includes the actuator handle assembly 210. The actuator handle assembly 200 can share features with the actuator handle assembly 110. For example, the actuator handle assembly 210 includes a housing 211 and an internal carriage assembly 245 (FIGS. 34-35) that translates along an actuator slot 213. In some embodiments, a user can grasp the actuator 216 to urge movement along the actuator slot 213, which causes the internal carriage assembly 245 to slidably translate along the longitudinal axis of the handle assembly 210, as indicated by the arrow 215. In some embodiments the carriage assembly can be translated, without limitation, about 8 cm to about 12 cm, or about 6 cm to about 10 cm, or about 4 cm to about 8 cm, or about 6 cm to about 14 cm. As the carriage assembly is translated in relation to the housing 211, the drive shaft 236 translates in relation to the sheath 232 in a corresponding manner. As previously described, the actuator 216 of the handle assembly 210 includes a rotational power button that can activate the electrical motor 212 (carried by the internal carriage assembly) to drive the rotation of the drive shaft 236. As such, by reciprocating actuator 216 and engaging the power button, the user can reciprocate the distal end portion of the drive shaft 236 in distal and proximal directions relative to the stenotic lesion 207 while the abrasive elements 240*a-c* are rotated in an orbital path and positioned distally of a distal most end of the sheath 232. Additionally, the user can retract and extend the distal portion of the drive shaft 236 (including the abrasive elements 240*a-c*) relative to the distal end of the sheath 232 to retract the abrasive elements 240*a-c* into the sheath 232 and to extend the abrasive elements 240*a-c* from the distal end of the sheath 232 to expose the abrasive elements 240*a-c*.

The handle assembly 210 has the cable connection 121 with the power adapter 120 (configured to receive electrical power from a power source 128 such as a wall plug) and fluid line connection 126 with a saline source 125. The cable 121 can communicate both power and data (e.g., when the controller 150 is housed within the power adapter housing 122), or alternatively, can communicate electrical power (e.g., when implementing the version with the controller 250A that is housed in the handle housing 211). The cable 121 includes a removable connection jack so that the handle assembly 210 can be readily discarded after a single use and the power adapter 120 can be reused with subsequent handle assemblies. The fluid line connection 126 can include a luer fitting and a flow on-off valve so that a user can removably connect the handle assembly to a pole-mounted saline bag or other fluid source 125 without the need for an external pump mechanism positioned exterior to the handle housing 211.

Referring to FIGS. 27-35, in operation of the system 200, a user can translate the actuator 216 of the handle assembly 210 in the actuator slot 213 so as to retract and extend the abrasive elements 240*a-c* from the distal end of the sheath 232. For example, the retraction of the abrasive elements 240*a-c* within the sheath 232 can advantageously cover the abrasive surfaces during navigation of abrasive elements 240*a-c* to the target area, thereby reducing the likelihood of scraping or engaging unintended regions of a vessel along the navigation path. The user can then selectively adjust the abrasive elements 240*a-c* distally from the sheath 232 lumen after navigating to the targeted site (e.g., for rotational atherectomy treatment). Also as described in more detail below, the system 200 can be configured to automatically prevent of rotation of the drive shaft 236 when the abrasive elements 240*a-c* are retracted within the sheath lumen (FIGS. 28-29) and to provide selective activation of rotation of the drive shaft when the abrasive elements are in an extended position (e.g., FIGS. 30-31 and 32-33). Accordingly, the system 200 can provide an added safety control that facilitates improved and intuitive operation for a user both during navigation and during rotational atherectomy treatment.

In some embodiments, the user can grasp the actuator 216 to urge movement along the actuator slot 213, which causes the internal carriage assembly 245 to slidably translate along the longitudinal axis of the handle assembly 210, as indicated by the arrow 215 to various positions within the actuator slot 213. As the carriage assembly 245 is translated in relation to the housing 211, the drive shaft 236 translates in relation to the sheath 232 in a corresponding manner. As such, the user can retract and extend the distal portion of the drive shaft 236 (including the abrasive elements 240*a-c*) relative to the distal end of the sheath 232. For example, the user can translate the actuator 216 proximally to the position of FIGS. 28, 29, and 35 to retract the abrasive elements 240*a-c* into the sheath 232.

Figure 35:
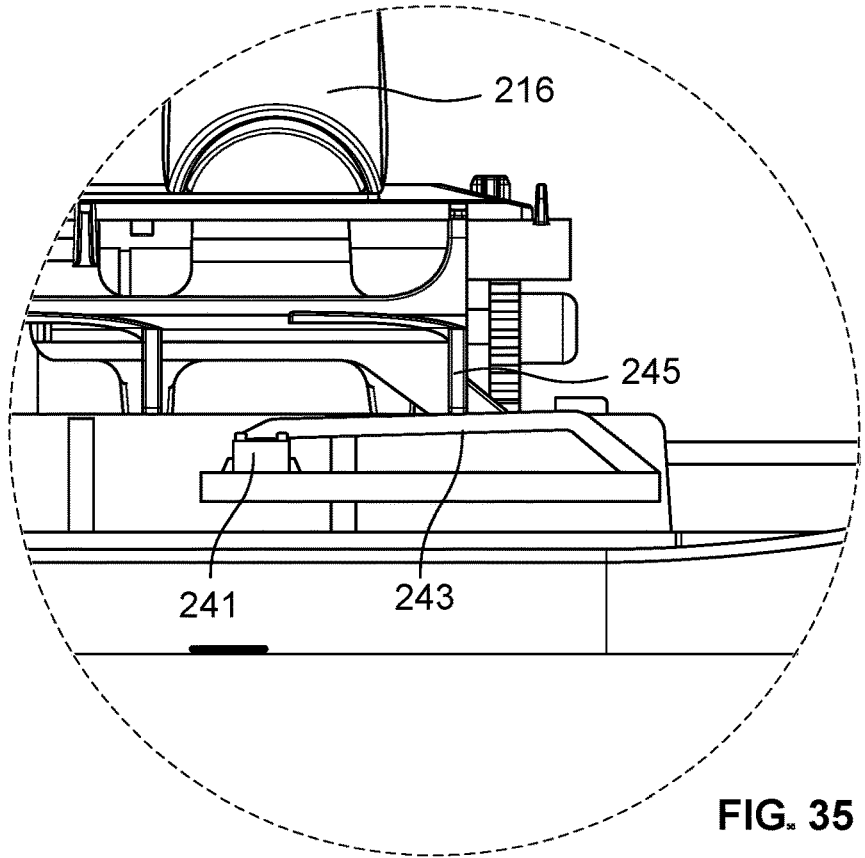
FIG. 35 is a detailed sectional view area 34 of the rotational atherectomy system from FIG. 28.

In the proximal position depicted in FIGS. 28, 29, and 35, the abrasive elements 240*a-c* are retracted and housed within the distal end of the sheath 232. The sheath 232 covering the abrasive elements 240*a-c* facilitates navigation to and from a targeted small artery, including those where the vessel interior diameter is often 3 mm or less and the access path follows a tortuous route. For example, sheath 232 can include a smooth outer surface that facilitates ease of navigation and protection of the tortuous route that is not the targeted area (e.g., prevents the abrasive elements 240*a-c* from engaging with areas outside of the target area).

Responsive to translation of the actuator 216 into the proximal position depicted in FIGS. 28, 29, and 35, power is not supplied to the electrical motor 212 regardless of whether the rotational power button of the actuator 216 is actuated. For example, the handle assembly 210 can include a switch 241 (FIG. 35) that controls power delivery to the electrical motor 212. In some embodiments, the switch 241 is at least one of a mechanical switch, an optical switch, a magnetic switch, a rotary switch, a push button, or combinations thereof. In the proximal position, the carriage assembly 245 connected to the actuator 216 slides proximally and contacts a switch arm 243 to depresses the switch 241. With the switch 241 depressed, power is not delivered to the electrical motor 212 and rotation of the drive shaft 236 is prevented. As such, with the abrasive elements 240a-c retracted within the sheath 232, the drive shaft 236 and abrasive elements 240a-c are prevented from rotation while the abrasive elements 240a-c are retracted within the sheath 232. The prevention of rotation of the drive shaft 236 and abrasive elements 240a-c (which can be executed by the controller described above) advantageously reduce the likelihood one or more abrasive elements 240a-c from abrading an interior of the sheath 232. Accordingly, in the proximal position, if a user presses the power button, power will not be supplied to the electric motor 212, and the drive shaft 236 will not rotate.

Figure 34:
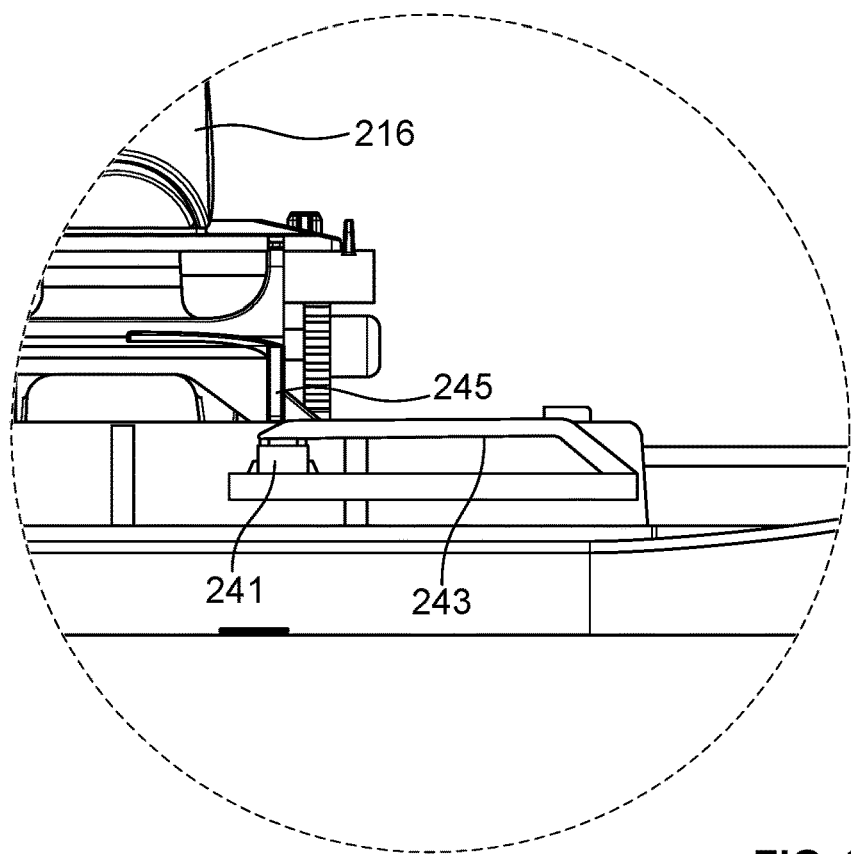
FIG. 34 is a detailed sectional view area 34 of the rotational atherectomy system from FIG. 30.

In the threshold position depicted in FIGS. 30, 31, and 34, the abrasive elements 240a-c are extended out of the distal end of the sheath 232 to a minimum distance from the distal end of the sheath 232 where the abrasive elements 240a-c are permitted to rotate and revolve in an orbital path to thereby contact and remove portions of a target lesion 207 (even those portions of the lesion that are spaced farther from the axis of the drive shaft 236 than the maximum radius of the abrasive elements 240a-c).

Still referring to FIGS. 27-35, responsive to translation of the actuator 216 into the threshold position depicted in FIGS. 30, 30, and 34, power is supplied to the electrical motor 212. For example, in the threshold position, the carriage assembly 245 connected to the actuator 216 slides distally and releases contact with the switch arm 243 and disengages the switch 241. With the switch 241 disengaged, power is delivered to the electrical motor 212 and rotation of the drive shaft 236 is permitted when the user presses the power button. Accordingly, in the threshold position, responsive to a user pressing the power button, power is supplied to the electric motor 212, and the drive shaft 236 rotates.

In the distal position depicted in FIGS. 32 and 33, the abrasive elements 240a-c are extended further from the distal end of the sheath 232 to a maximum distance from the distal end of the sheath 232 where the abrasive elements 240a-c are permitted to rotate and revolve in an orbital path to thereby contact and remove portions of a target lesion 207 (even those portions of the lesion that are spaced farther from the axis of the drive shaft 236 than the maximum radius of the abrasive elements 240a-c).

Responsive to translation of the actuator 216 into the distal position depicted in FIGS. 30, 30, and 34, the electrical motor 212 remains connected to power. For example, in the distal position, the carriage assembly 245 connected to the actuator 216 slides further distally and the switch arm 243 remains disengaged from the switch 241. With the switch 241 disengaged, power is delivered to the electrical motor 212 and rotation of the drive shaft 236 is permitted when the user presses the power button. Accordingly, in the distal position, responsive to a user pressing the power button, power is supplied to the electric motor 212, and the drive shaft 236 rotates. In some embodiments, contemporaneous with the rotation of the drive shaft 236, the drive shaft 236 can be translated back and forth (distally and proximally) along the longitudinal axis of the drive shaft 236 between the threshold position and the distal position. Hence, the stenotic lesion 207 can be abraded radially and longitudinally by virtue of the simultaneous translation and orbital rotation of the abrasive elements 240a-c. If the user translates the actuator 216 proximally past the threshold position, power to the electric motor 212 is stopped, and rotation of the abrasive elements 240a-c also stops.

To operate the handle assembly 210 during a rotational atherectomy procedure, a clinician can grasp the actuator 216, actuate (translate) the actuator 216 to a position at or distal of the threshold position shown in FIGS. FIGS. 30, 31, and 34 and depress rotational power button (on the actuator 216) with the same hand. During the actuation or translation of the actuator 216 distally (e.g., from the proximal position shown in FIGS. 28, 29, and 35), the abrasive elements 240a-c are advanced distally out of the distal end of the sheath 232 and are exposed to the target area. Additionally, the switch 241 is disengaged and power is supplied to the electric motor 217. The clinician can move (translate) the actuator 116 along the slot 213 distally and proximally by hand (e.g., back and forth in relation to the housing 211), while maintaining the rotational power button of the actuator 216 in the depressed state and while maintaining the abrasive elements 240a-c at a position beyond the distal end of the sheath 232. In that manner, a target lesion 207 can be abraded radially and longitudinally by virtue of the resulting orbital rotation and translation of the abrasive elements 240a-c.

To further operate the handle assembly 210 during a rotational atherectomy procedure, a clinician can select a rotational speed using electrical switches 217a and 217b. In some cases, the rotational speed can be selected through a set of predefined speeds (e.g., at least two predefined speed settings, such as "low" and "high") with electrical switch 217a causing an increase in the speed setting and electrical switch 217b causing a decrease in the speed setting. Optionally, each of the electrical switches 217a-b can also include a light indicator. For example, when the electrical switches 217a-b allow for selection for a "high" and "low" speed, respectively, the electrical switches 217a-b can each have a single light, such that when a speed is selected, the light corresponding to the selected electrical switch 217a or 217b is illuminated to inform a clinician of the selected speed. In some embodiments, the light can shine through electrical switches 217 and 217b. Alternatively, a light can be positioned proximal electrical switch 217a-b. As another example, when the electrical switches 217a-b allow modification of a speed between a range of speeds, the light indicator can be a light bar, such that a number of lights illuminated on the light bar correspond to a selected speed.

Still referring to FIGS. 27-35, to further operate the handle assembly 210, the handle assembly 210 can include a fluid pump switch 217c. The fluid pump switch 217c can share the features of fluid pump switch 117c such as activating the internal fluid pump 214 to draw fluid (e.g., saline in this embodiment) from the fluid line 126 and urge the fluid through the sheath 232 toward the distal end portion of the drive shaft 236. As such, the fluid pump switch 217c can be used to both initially prime the sheath 232 (and remove air before insertion into the patient) and then selectively activate additional flush fluid through the sheath 232 and into the vessel 205. In some cases, a first depression of the fluid pump switch 217c will turn the internal pump 214 on, while a second depression will turn the pump 214 off. In some embodiments, the fluid pump switch 217c includes a light indicator, such that when the pump is on, a light is illuminated to inform the clinician that the pump is on.

In the depicted embodiment, the handle assembly 210 also includes a guidewire brake 218 that can share features with the guidewire brake 118. For example, the guidewire brake 218 can be selectively actuated (e.g., pivoted relative to the handle housing 211 in this embodiment) to releasably clamp the guidewire 234 in a stationary position relative to the handle assembly 210 (and, in turn, stationary in relation to rotations of the drive shaft 236 during an atherectomy treatment). While the drive shaft 236 and handle assembly 210 are being advanced over the guidewire 234 to put the one or more abrasive elements 238 into a targeted position within a patient's vessel, the guidewire brake 218 is in a non-activated state (e.g., pivoted counter-clockwise about the central guidewire axis) from a rear perspective) so that the handle assembly 210 is free to slide in relation to the guidewire 234. Then, when the clinician is ready to begin the atherectomy treatment, the guidewire brake 218 can be activated (e.g., pivoted clockwise about the central guidewire axis) to mechanically engage an exterior of the guidewire 234 and thereby releasably detain/lock the guidewire 234 in relation to the handle assembly 210. That way, the guidewire 234 will not rotate while the drive shaft 236 is rotating, and the guidewire 234 will not translate while the actuator 216 is being manually translated in the direction 215.

In some embodiments, the handle assembly 110 can include a guidewire brake light 219 that positioned along an upper face of the handle housing 211 at a position proximal to the other user interface buttons 217a-c and adjacent to the guidewire brake 218. As such, a user can readily view the guidewire brake light 219 (e.g., similar to the guidewire brake light 119) and receive confirmation of whether the guidewire brake 218 is fully activated (to clamp the guidewire 234) before selecting the rotational speed (e.g., buttons 217a-b) and activating rotation (e.g., button on the actuator 216). As such, the screenless user interface of the handle assembly 210 can provide a simplified and fluid hand motion for the user while also communicating effective information to the user.

Optionally, the controller 250 (or 250A in other embodiments) can be configured to prevent the electric motor 212 from driving rotation of the drive shaft 236 until: (1) the guidewire brake 218 is activated (e.g., with the guidewire brake light 119 illuminated), (2) the pump 214 is activated to drive the flush fluid (e.g., via actuation of fluid pump switch 117c that then illuminates the button 117c), (3) a rotation speed has been selected via speed selection switches 217a and 217b (e.g., with a speed indicator light thereon being activated), (4) when the switch 241 is disengaged in response to the position of the actuator 216, or a combination of all these conditions. As another example, the indicator lights associated with the selection switches 217a and 217b, the fluid pump switch 217c, and the guidewire brake light 219 will alert a clinician that the rotational atherectomy system 200 should not be operated until all four systems (the position of the actuator, the motor, the pump, the guidewire brake) are activated and in position for use. For example, each system may have a green light, such that three green lights indicates the clinician can proceed with the atherectomy procedure. Optionally, only (1) the switch 241 is disengaged and (2) the guidewire 118 is actuated to allow rotation of the rotational atherectomy system 200. Optionally, only the switch 241 is disengaged to allow rotation of the rotational atherectomy system 200.

Still referring to FIGS. 27-35, the rotational atherectomy system 200 also includes the controller 150, which in this embodiment includes a processor and computer-readable memory storing control instructions thereon. The controller 150 is configured to receive input from sensors housed within the handle assembly, to receive input from the user interface on the handle assembly 210 (e.g., switches/actuators 216, 217a-c, 218, and 241), and to control the activation of the electric motor 212 and the pump 214 (responsive to inputs at the user interface switches/actuators). In this embodiment, the controller 150 is contained inside the housing 122 of the power adapter 120 so that it is reusable with subsequent handle assemblies after the first handle assembly 210 is discarded (e.g., after use with a first patient). As previously described, the cable 121 can provide data communication between the controller 150 and the components of the user interface (e.g., switches/actuators 216, 217a-c, 218, and 241), the electric motor 212, the pump 214, and the feedback sensors housed within the handle assembly 210. In an alternative embodiment, the controller (including the processor and computer-readable memory storing the control instructions) can be provided in the form of controller 250A configured to be contained within the housing 211 of the handle assembly 210 (in proximity to the electric motor 212 and the pump 214). In both options, the handle assembly 210 can be operated by a clinician using the above-described simplified, screenless interface to perform and control the rotational atherectomy procedure (e.g., without a user interface display screen along the handle assembly or on the units connected to the handle assembly). Preferably, the controller 150 (or controller 250A) is housed in a manner that is sealed from fluids encountered by the handle assembly, such as saline, blood, or others.

A number of embodiments of the invention have been described. Nevertheless, it will be understood that various modifications may be made without departing from the spirit and scope of the invention. For example, design features of the embodiments described herein can be combined with other design features of other embodiments described herein. Accordingly, other embodiments are within the scope of the following claims.

What is claimed is:
1. A rotational atherectomy system for removing stenotic lesion material from a pedal artery or coronary artery of a patient, comprising:
a 4-French introducible rotational atherectomy device, comprising:
a torque-transmitting coil of one or more filars that are helically wound around in a filar wind direction from a distal end to a proximal end to define a coil diameter and a drive shaft axis, wherein the torque-transmitting coil has an outer coil diameter and each abrasive burr in the series of abrasive burrs has a respective burr diameter, wherein a burr-to-coil diameter ratio define by each respective burr diameter and the outer coil diameter is about 1.2-1.7; and
a series of abrasive burrs fixedly mounted to a distal end portion of the torque-transmitting coil and having a maximum burr diameter of no greater than 1.25 mm, wherein the series of abrasive burrs includes a distal concentric abrasive burr coaxially mounted to a distal-most end of the torque-transmitting coil, a proximal concentric abrasive burr having the same size as the distal concentric abrasive burr and being coaxially mounted to the torque-transmitting coil at a position no greater than 0.5-inches from the distal-most end of the torque-transmitting coil, and an intermediate eccentric abrasive burr having a larger size than the distal and proximal concentric abrasive burrs and being mounted to the torque-transmitting coil with a center of mass offset from the drive shaft axis; and
a rotational atherectomy handle assembly coupled to the proximal end of the torque-transmitting coil and housing an electric motor configured to, responsive to user input at an actuator of the rotational atherectomy handle assembly, drive rotation of the series of abrasive burrs about the drive shaft axis in a rotational direction.

2. The rotational atherectomy system claim 1, further comprising a sheath that extends from the rotational atherectomy handle assembly and over the torque transmitting coil, wherein the actuator of the rotational atherectomy handle assembly is configured to longitudinally adjust the torque-transmitting coil relative to the sheath such that, in a proximal position, the series of abrasive burrs are housed within a distal-most end of the sheath.

3. The rotational atherectomy system of claim 2, wherein responsive to distal longitudinal movement of the actuator of the rotational atherectomy handle, the series of abrasive burrs are adjusted to a distal position so as to extend distally from the distal-most end of the sheath.

4. The rotational atherectomy system of claim 3, wherein the electric motor housed within the rotational atherectomy handle is prevented from rotating the torque-transmitting coil when the series of abrasive burrs are in the proximal position and housed within the distal-most end of the sheath.

5. The rotational atherectomy system of claim 4, wherein when the series of abrasive burrs are adjusted to the distal position to extend distally from the distal-most end of the sheath, a switch that is housed within the rotational atherectomy handle is triggered and the electric motor is selectively activatable to drive rotation of the series of abrasive burrs.

6. The rotational atherectomy system of claim 5, wherein when the actuator of the rotational atherectomy handle assembly is adjusted to a location proximal of a threshold position along an upper face of the rotational atherectomy handle assembly, the series of abrasive burrs are in the proximal position and housed within the distal-most end of the sheath.

7. The rotational atherectomy system of claim 6, wherein when the actuator of the rotational atherectomy handle assembly is adjusted to a location distal of the threshold position along the upper face of the rotational atherectomy handle assembly, the series of abrasive burrs are in the distal position and extend distally from the distal-most end of the sheath.

8. The rotational atherectomy device of claim 5, wherein contemporaneous with selective activation to drive rotation of the series of abrasive burrs, the torque transmitting coil is selectively translatable distally and proximally along the drive shaft axis.

9. The rotational atherectomy device of claim 8, further comprising a power button at the rotational atherectomy handle assembly that is selectable to activate the electric motor.

10. The rotational atherectomy device of claim 9, wherein, responsive to selection of the power button with the series of abrasive burrs in the distal position, the electric motor activates to drive rotation of the series of abrasive burs.

11. The rotational atherectomy device of claim 2, wherein the torque transmitting coil is laterally flexible.

12. The rotational atherectomy device of claim 11, wherein the sheath includes a radiopaque marker at a distal end of the sheath.

13. The rotational atherectomy system of claim 1, wherein a diameter of the proximal concentric abrasive burr is equal to a diameter of the distal concentric abrasive burr, and the diameter of the proximal and distal concentric abrasive burrs is less than a diameter of the intermediate eccentric abrasive burr.

14. The rotational atherectomy system of claim 13, wherein a diameter of the intermediate eccentric abrasive burr is 1.25 mm and a diameter of each of the proximal and distal concentric abrasive burrs is 1.1 mm.

15. The rotational atherectomy system of claim 14, wherein each abrasive burr of the series of abrasive burrs is a spherical metallic burr coated with diamond grit.

16. The rotational atherectomy system of claim 1, wherein the electric motor housed within the rotational atherectomy handle assembly is configured to rotate the torque-transmitting coil so that the series of abrasive burrs orbit in the rotational direction opposite of the filar wind direction.

17. The rotational atherectomy device of claim 1, further comprising a concentric tip member positioned distally of the distal concentric abrasive burr.

18. The rotational atherectomy device of claim 17, wherein the concentric tip member comprises a smoother outer surface than the series of abrasive burrs.

19. A rotational atherectomy system for removing stenotic lesion material from a pedal artery or coronary artery of a patient, comprising:
a 4-French introducible rotational atherectomy device, comprising:
a torque-transmitting coil of one or more filars that are helically wound around in a filar wind direction from a distal end to a proximal end to define a coil diameter and a drive shaft axis; and
a series of abrasive burrs fixedly mounted to a distal end portion of the torque-transmitting coil and having a maximum burr diameter of no greater than 1.25 mm, wherein the series of abrasive burrs includes a distal concentric abrasive burr coaxially mounted to a distal-most end of the torque-transmitting coil, a proximal concentric abrasive burr having the same size as the distal concentric abrasive burr and being coaxially mounted to the torque-transmitting coil at a position no greater than 0.5-inches from the distal-most end of the torque-transmitting coil, and an intermediate eccentric abrasive burr having a larger size than the distal and proximal concentric abrasive burrs and being mounted to the torque-transmitting coil with a center of mass offset from the drive shaft axis; and
a rotational atherectomy handle assembly coupled to the proximal end of the torque-transmitting coil and housing an electric motor configured to, responsive to user input at an actuator of the rotational atherectomy handle assembly, drive rotation of the series of abrasive burrs about the drive shaft axis in a rotational direction; and
a sheath that extends from the rotational atherectomy handle assembly and over the torque transmitting coil, wherein the actuator of the rotational atherectomy handle assembly is configured to longitudinally adjust the torque-transmitting coil relative to the sheath such that, in a proximal position, the series of abrasive burrs are housed within a distal-most end of the sheath,
wherein responsive to distal longitudinal movement of the actuator of the rotational atherectomy handle, the series of abrasive burrs are adjusted to a distal position so as to extend distally from the distal-most end of the sheath,
wherein the electric motor housed within the rotational atherectomy handle is prevented from rotating the torque-transmitting coil when the series of abrasive burrs are in the proximal position and housed within the distal-most end of the sheath,
wherein when the series of abrasive burrs are adjusted to the distal position to extend distally from the distal-most end of the sheath, a switch that is housed within the rotational atherectomy handle is triggered and the electric motor is selectively activatable to drive rotation of the series of abrasive burrs, wherein when the actuator of the rotational atherectomy handle assembly is adjusted to a location proximal of a threshold position along an upper face of the rotational atherectomy handle assembly, the series of abrasive burrs are in the proximal position and housed within the distal-most end of the sheath; and a power button at the rotational atherectomy handle assembly that is selectable to activate the electric motor, wherein the electric motor remains disengaged responsive to selection of the power button with the series of abrasive burrs in the proximal position.

* * * * *